(12) United States Patent
Li et al.

(10) Patent No.: US 12,091,432 B2
(45) Date of Patent: Sep. 17, 2024

(54) COMPOUNDS AND METHODS FOR SYNTHESIZING SPHINGOSINES AND GLYCOLIPIDS

(71) Applicant: GEORGIA STATE UNIVERSITY RESEARCH FOUNDATION, INC., Atlanta, GA (US)

(72) Inventors: Lei Li, Alpharetta, GA (US); George Peng Wang, Johns Creek, GA (US); Madhusudhan Reddy Gadi, Atlanta, GA (US); Jun Yin, Atlanta, GA (US)

(73) Assignee: GEORGIA STATE UNIVERSITY RESEARCH FOUNDATION, INC., Atlanta, GA (US)

( * ) Notice: Subject to any disclaimer, the term of this patent is extended or adjusted under 35 U.S.C. 154(b) by 62 days.

(21) Appl. No.: 17/677,227

(22) Filed: Feb. 22, 2022

(65) Prior Publication Data
US 2022/0275016 A1  Sep. 1, 2022

Related U.S. Application Data

(60) Provisional application No. 63/154,921, filed on Mar. 1, 2021.

(51) Int. Cl.
*C07H 15/10* (2006.01)

(52) U.S. Cl.
CPC .................................. *C07H 15/10* (2013.01)

(58) Field of Classification Search
None
See application file for complete search history.

(56) References Cited

U.S. PATENT DOCUMENTS 9,708,354 B2  7/2017 Oniciu

OTHER PUBLICATIONS

Sridhar et al., Tetrahedron, 2009, vol. 65(51), pp. 10701-10708. (Year: 2009).*
Kobayashi et al., Journal of American Chemical Society, 2004, 126(30), pp. 9192-9193. (Year: 2004).*
Azuma, H.; Tamagaki, S.; Ogino, K. "Stereospecific Total Syntheses of Sphingosine and Its Analogues from L-Serine". *J. Org. Chem.* 2000, 65, 3538-3541.
Bremer, E. G.; Schlessinger, J.; Hakomori, S. "Ganglioside Mediated Modulation of Cell Growth. Specific Effects of GM3 on Tyrosine Phosphorylation of the Epidermal Growth Factor Receptor". *J. Biol. Chem.* 1986, 261, 2434-2440.
Bremer, E. G.; Hakomori, S.; Bowen-Pope, D. F.; Raines, E.; Ross, R. "Ganglioside Mediated Modulation of Cell Growth, Growth Factor Binding, and Receptor Phosphorylation". *J. Biol. Chem.* 1984, 259, 6818-6825.
Boons, G. J. P. H.; van Delft, F. L.; van der Klein, P. A. M.; van der Marel, G. A.; van Boom, J. H. "Synthesis of ld-Hepp and KDO Containing Di- and Tetrasaccharide Derivatives of *Neisseria meningitidis* Inner-Core Region via Iodonium Ion Promoted Glycosidations". *Tetrahedron* 1992, 48, 885-904.
Carr, A.; Rodríguez, E.; del Carmen Arango, M.; Camacho, R.; Osorio, M.; Gabri, M.; Carrillo, G.; Valdés, Z.; Bebelagua, Y.; Pérez, R.; Fernández, L. E. "Immunotherapy of Advanced Breast Cancer with a Heterophilic Ganglioside (NeuGcGM3) Cancer Vaccine". *J. Clin. Oncol.* 2003, 21, 1015-1021.
Cavdarli, S.; Dewald, J. H.; Yamakawa, N.; Guérardel, Y.; Terme, M.; Le Doussal, J.-M.; Delannoy, P.; Groux-Degroote, S. "Identification of 9-O-Acetyl-N-acetylneuraminic Acid (Neu5,9Ac2) as Main O-Acetylated Sialic Acid Species of GD2 in Breast Cancer Cells". *Glycoconjugate J.* 2019, 36, 79-90.
Cheever, M. A.; Allison, J. P.; Ferris, A. S.; Finn, O. J.; Hastings, B. M.; Hecht, T. T.; Mellman, I.; Prindiville, S. A.; Viner, J. L.; Weiner, L. M.; Matrisian, L. M. "The Prioritization of Cancer Antigens: a National Cancer Institute Pilot Project for the Acceleration of Translational Research". *Clin. Cancer Res.* 2009, 15, 5323-5337.
Cutillo, G.; Saariaho, A.-H.; Meri, S. "Physiology of Gangliosides and the Role of Antiganglioside Antibodies in Human Diseases". *Cell. Mol. Immunol.* 2020, 17, 313-322.
D'angelo, G.; Capasso, S.; Sticco, L.; Russo, D. "Glycosphingolipids: Synthesis and Functions". *FEBS J.* 2013, 280, 6338-6353.
Dam, D. H. M.; Paller, A. S. "Gangliosides in Diabetic Wound Healing". *Prog. Mol. Biol. Transl. Sci.* 2018, 156, 229-239.
De La Torre, A.; Hernandez, J.; Ortiz, R.; Cepeda, M.; Perez, K.; Car, A.; Viada, C.; Toledo, D.; Guerra, P. P.; García, E.; Arboláez, M.; Fernandez, L. E. "NGlycoly1GM3/VSSP Vaccine in Metastatic Breast Cancer Patients: Results of Phase I/IIa Clinical Trial". *Breast Cancer* 2012, 6, 151-157.
De La Torre, A.; Pérez, K.; Vega, A. M.; Santiesteban, E.; Ruiz, R.; Hernández, L.; Durruti, D.; Viada, C. E.; Sánchez, L.; Alvarez, M.; Durán, Y.; Moreno, Y. G.; Arencibia, M.; Cepeda, M.; Domecq, M.; Cabrera, L.; Sánchez, J. L.; Hernández, J. J.; Valls, A. R.; Fernández, L. E. "Superior Efficacy and Safety of a Nonemulsive Variant of the NGcGM3/VSSP Vaccine in Advanced Breast Cancer Patients". *Breast Cancer* 2016, 10, 5-11.
Dondoni, A.; Perrone, D. "Synthesis of 1,1-Dimethylethyl (S)-4-Formyl-2,2-Dimethyl-3-Oxazolidinecarboxylate by Oxidation of the Alcohol". *Org. Synth.* 2000, 77, 64-77.
Estevez, F.; Carr, A.; Solorzano, L.; Valiente, O.; Mesa, C.; Barroso, O.; Victoriano Sierra, G.; Fernandez, L. E. "Enhancement of the Immune Response to Poorly Immunogenic Gangliosides After Incorporation into Very Small Size Proteoliposomes (VSSP)". *Vaccine* 1999, 18, 190-197.
Fernandez, L. E.; Gabri, M. R.; Guthmann, M. D.; Gomez, R. E.; Gold, S.; Fainboim, L.; Gomez, D. E.; Alonso, D. F. "NGcGM3 Ganglioside: a Privileged Target for Cancer Vaccines". *Clin. Dev. Immunol.* 2010, 814397.

(Continued)

*Primary Examiner* — Traviss C McIntosh, III
(74) *Attorney, Agent, or Firm* — MUETING RAASCH GROUP

(57) ABSTRACT

The present disclosure is concerned with compounds, compositions, and methods for synthesizing sphingosines and glycolipids including glycosphingolipids, such as but not limited to lactosyl sphingosine.

16 Claims, 6 Drawing Sheets

(56) References Cited

OTHER PUBLICATIONS

Garner, P.; Park, J. M.; Malecki, E. "A Stereodivergent Synthesis of D-Erythro-Sphingosine and D-Threo-Sphingosine from L-Serine". *J. Org. Chem.* 1988, 53, 4395-4398.
Gao et al., *Synthesis*, 2016, 48, 4017-4037.
Ghosh, A.; Chattopadhyay, S. K. "A Diversity Oriented Synthesis of D-Erythro-Sphingosine and Siblings". *Tetrahedron: Asymmetry* 2017, 28, 1139-1143.
Hafner, A.; Duthaler, R. O.; Marti, R.; Rihs, G.; Rothe-Streit, P.; Schwarzenbach, F. "Enantioselective Syntheses with Titanium Carbohydrate Complexes. Part 7. Enantioselective Allyltitanation of Aldehydes with Cyclopentadienyldialkoxyallyltitanium Complexes". *J. Am. Chem. Soc. 1992*, 114, 2321-2336.
Hayashi, N.; Chiba, H.; Kuronuma, K.; Go, S.; Hasegawa, Y.; Takahashi, M.; Gasa, S.; Watanabe, A.; Hasegawa, T.; Kuroki, Y.; Inokuchi, J.; Takahashi, H. "Detection of N-Glycolyated Gangliosides in Non-Small-Cell Lung Cancer Using GMR8 Monoclonal Antibody". *Cancer Sci.* 2013, 104, 43-47.
Hunter et al., *Chemical Reviews*, 2018, 118, 8188-8241.
Inamori, K.-i.; Inokuchi, J.-i. "Roles of Gangliosides in Hypothalamic Control of Energy Balance: New Insights". *Int. J. Mol. Sci.* 2020, 21, 5349.
Kim et al., *The Journal of Organic Chemistry* 2006, 71, 8661-8664.
Koskinen, P. M.; Koskinen, A. M. P. "Total Synthesis of Sphingosine and Its Analogs". *Methods Enzymol.* 2000, 311, 458-479.
Koolath et al., *Chirality* 2020, 32, 308-313.
Labrada, M.; Dorvignit, D.; Hevia, G.; Rodríguez-Zhurbenko, N.; Hernández, A. M.; Vázquez, A. M.; Fernández, L. E. "GM3-(Neu5Gc) Ganglioside: an Evolution Fixed Neoantigen for Cancer Immunotherapy". *Semin. Oncol.* 2018, 45, 41-51.
Liu et al., *European Journal of Organic Chemistry*, 2016, 2016, 4315-4320.
Li, Y.; "Pasteurella multocida CMP-sialic acid synthetase and mutants of Neisseria meningitidis CMP-sialic acid synthetase with improved substrate promiscuity" Appl Microbiol Biotechnol, 2012, 93:2411-2423.
Li, Y.; Arigi, E.; Eichert, H.; Levery, S. B. "Mass Spectrometry of Fluorocarbon-Labeled Glycosphingolipids". *J. Mass Spectrom.* 2010, 45, 504-519.
Mulens, V.; de la Torre, A.; Marinello, P.; Rodríguez, R.; Cardoso, J.; Díaz, R.; O'Farrill, M.; Macias, A.; Viada, C.; Saurez, G.; Carr, A.; Crombet, T.; Mazorra, Z.; Perez, R.; Fernández, L. E. "Immunogenicity and Safety of a NeuGcGM3 Based Cancer Vaccine: Results from a Controlled Study in Metastatic Breast Cancer Patients". *Hum. Vaccines 2010*, 6, 736.
Park, E. J.; Suh, M.; Ramanujam, K.; Steiner, K.; Begg, D.; Clandinin, M. T. "Diet-Induced Changes in Membrane Gangliosides in Rat Intestinal Mucosa, Plasma and Brain". *J. Pediatr. Gastroenterol. Nutr.* 2005, 40, 487-495.
Santra, A.; Li, Y.; Yu, H.; Slack, T. J.; Wang, P. G.; Chen, X. "Highly Efficient Chemoenzymatic Synthesis and Facile Purification of alpha-Gal Pentasaccharyl Ceramide Galalpha3nLc4betaCer". *Chem. Commun.* 2017, 53, 8280-8283.
Schnaar, R. L.; Kinoshita, T. "Glycosphingolipids. in Essentials of Glycobiology"; Varki, A., Cummings, R. D., Esko, J. D., Stanley, P.; Hart, G. W., Aebi, M., Darvill, A. G., Kinoshita, T., Packer, N. H., Prestegard, J. H., Schnaar, R. L., Seeberger, P. H., Eds .; *Cold Spring Laboratory Press*: NY, 2015; pp. 125-135.
Scursoni, A. M.; Galluzzo, L.; Camarero, S.; Lopez, J.; Lubieniecki, F.; Sampor, C.; Segatori, V. I.; Gabri, M. R.; Alonso, D. F.; Chantada, G.; de Dávila, M. T. "Detection of N-Glycolyl GM3 Ganglioside in Neuroectodermal Tumors by Immunohistochemistry: an Attractive Vaccine Target for Aggressive Pediatric Cancer". *Clin. Dev. Immunol.* 2011, 245181.
Shapiro and Segal, *Journal of the American Chemical Society* 1954, 76, 5894-5895.
Sonnino, S.; Chigorno, V. "Ganglioside Molecular Species Containing C18- and C20-Sphingosine in Mammalian Nervous Tissues and Neuronal Cell Cultures". *Biochim. Biophys. Acta* 2000, 1469, 63-77.
Sridhar, R.; Srinivas, B.; Rama Rao, K. "Asymmetric synthesis of triacetyl-D-erythro-sphingosine and D-1-deoxyallonojirimycin via Miyashita C2 selective endo-mode azide opening of 2,3-epoxy alcohol." *Tetrahedron* 2009, 65, 10701-10708.
Torssell and Somfai, *Organic & Biomolecular Chemistry*, 2004, 2, 1643-1646.
Tagami, S.; Inokuchi, J.-i.; Kabayama, K.; Yoshimura, H.; Kitamura, F.; Uemura, S.; Ogawa, C.; Ishii, A.; Saito, M.; Ohtsuka, Y.; Sakaue, S.; Igarashi, Y. "Ganglioside GM3 Participates in the Pathological Conditions of Insulin Resistance" *J. Biol. Chem.* 2002, 277, 3085-3092.
Vankar et al., *Chemical Society Reviews*, 2000, 29, 201-216.
Veillon, L.; Go, S.; Matsuyama, W.; Suzuki, A.; Nagasaki, M.; Yatomi, Y.; Inokuchi, J.-i. "Identification of Ganglioside GM3 Molecular Species in Human Serum Associated with Risk Factors of Metabolic Syndrome". *PLoS One* 2015, 10, No. e0129645.
Wadsworth, "Synthetic Applications of Phosphoryl-Stabilized Anions". *In Organic Reactions*, 1977, pp. 73-253.
Wipfler, D.; Srinivasan, G. V.; Sadick, H.; Kniep, B.; Arming, S.; Willhauck-Fleckenstein, M.; Vlasak, R.; Schauer, R.; Schwartz-Albiez, R."Differentially Regulated Expression of 9-O-Acetyl GD3 (CD60b) and 7-O-Acetyl-GD3 (CD60c) During Differentiation and Maturation of Human T and B Lymphocytes". *Glycobiology* 2011, 21, 1161-1172.
Yoshida, M.; Saito, K.; Kato, H.; Tsukamoto, S.; Doi, T. "Total Synthesis and Biological Evaluation of Siladenoserinol A and Its Analogues". *Angew. Chem., Int. Ed.* 2018, 57, 5147-5150.
Yu et al., *The Journal of Organic Chemistry*, 2016, 81, 10809-10824.
Yu et al., *J. Org. Chem.* 2021, 86, 8672-8682.
Yu et al., *Org Biomol Chem*, 2018, 16, 4076-4080.
Yu, R. K.; Nakatani, Y.; Yanagisawa, M. "The Role of Glycosphingolipid Metabolism in The Developing Brain". *J. Lipid Res.* 2009, 50, S440-S445.
Zhang, et al., *Frontiers in Immunology*, 2019, 10.
Zhang et al., *Ann Clin Lab Sci*, 2004, 34, 3-13.
Zheng, C.; Terreni, M.; Sollogoub, M.; Zhang, Y. "Ganglioside GM3 and Its Role in Cancer". *Curr. Med. Chem.* 2019, 26, 2933-2947.

* cited by examiner

Scheme 1

Scheme 1, continued

Scheme 2

COMPOUNDS AND METHODS FOR SYNTHESIZING SPHINGOSINES AND GLYCOLIPIDS

CROSS-REFERENCE TO RELATED APPLICATIONS

This application claims the benefit of U.S. Provisional Application Ser. No. 63/154,921, filed Mar. 1, 2021, which is incorporated by reference herein in its entirety.

GOVERNMENT FUNDING

This invention was made with government support under U01GM120419 awarded by the National Institutes of Health. The government has certain rights in the invention.

BACKGROUND

Glycosphingolipids (GSLs) are a major class of glycolipids that are present on the surface of eukaryotic cells (Hunter et al., Chemical Reviews, 2018, 118, 8188-8241; Vankar et al., Chemical Society Reviews, 2000, 29, 201-216). They are a rich source of epitopes on cellular surfaces including the blood group antigens, and most of their biological functions are related to lipid-lipid and lipid-protein interactions. Over the past two decades, GSLs have been identified as playing many roles, including acting as messengers, ligands for selectins, maintaining cognitive functions, binding epitopes, and in maintaining the proper structure and functioning of cells (D'Angelo et al., The FEBS Journal, 2013, 280, 6338-6353; Zhang, et al., Frontiers in Immunology, 2019, 10; Zhang et al., Ann Clin Lab Sci, 2004, 34, 3-13). Most GSLs include a ceramide core containing D-Erythro-sphingosine (Sph), a C18 natural amino alcohol linked to a fatty acid chain via an amide linkage. Isolating GSLs from their natural sources in homogenous form requires laborious methods. Chemical and chemoenzymatic synthesis of GSLs often require Sph (Liu et al., European Journal of Organic Chemistry, 2016, 2016, 4315-4320; Yu et al., The Journal of Organic Chemistry, 2016, 81, 10809-10824; Yu et al., Org Biomol Chem, 2018, 16, 4076-4080), but producing pure Sph requires expensive materials or lengthy procedures (Gao et al., Synthesis, 2016, 48, 4017-4037). One route for synthesis of Sph begins with L-serine, but the method results in a racemic mixture which requires difficult steps to obtain high purity Sph.

SUMMARY OF THE APPLICATION

Recent advancements in understanding the biological role of glycosphingolipids (GSLs) led to the development of their synthesis using either chemical or chemoenzymatic routes. For each of these routes a pure suitably protected or unprotected sphingosine is required, which is often very expensive commercially (Torssell and Somfai, Organic & Biomolecular Chemistry, 2004, 2, 1643-1646) due to the difficulty in its isolation or presence of lengthy synthetic routes (Vankar and Schmidt, Chemical Society Reviews 2000, 29, 201-216). There are four stereo isomers of sphingosine (FIG. 1) and each isomer has different biological activities. Among them, D-erythro sphingosine (Sph) is the most common metabolite.

Sph was first isolated in 1884 from brain tissue and the first total synthesis was achieved in 1954 (Shapiro and Segal, Journal of the American Chemical Society 1954, 76, 5894-5895). Later, many synthetic routes were developed using either chiral or non-chiral substrates (Gao et al., Synthesis 2016, 48, 4017-4037) and the most prominent contemporary route is through commercially expensive D-ribo-phytosphingosine (Kim et al., The Journal of Organic Chemistry 2006, 71, 8661-8664), which is a sphingoid base significantly present in higher plants, yeast and fungi.

The present disclosure provides synthetic methods which permit the commercially viable large-scale synthesis of Sph. Specifically, provided herein are efficient stereoselective methods to synthesize Sph with high purity starting from a commercially inexpensive product, the amino acid serine.

Also provided by the present disclosure are methods for converting Sph to an acceptor compound and methods for employing the acceptor in the synthesis of sphingosines and glycolipids. In one embodiment, an acceptor disclosed herein can be used in the synthesis of lactosyl sphingosine, a compound that is a basic skeleton for use in the synthesis of GSLs (Yu et al., The Journal of Organic Chemistry, 2016, 81, 10809-10824).

Definitions

Terms used herein will be understood to take on their ordinary meaning in the relevant art unless specified otherwise. Several terms used herein and their meanings are set forth below.

As used herein, the term "organic group" means a hydrocarbon group (with optional elements other than carbon and hydrogen, such as oxygen, nitrogen, and sulfur) that is classified as an aliphatic group, cyclic group, or combination of aliphatic and cyclic groups (e.g., alkaryl and aralkyl groups). In the context of the present disclosure, the organic groups are those that do not interfere with the formation of the compounds described herein.

The terms "group" and "moiety" are used interchangeably.

The term "aliphatic group" means a saturated or unsaturated linear or branched hydrocarbon group. This term is used to encompass alkyl, alkenyl, and alkynyl groups, for example. An aliphatic group can be soluble in a nonpolar solvent. An aliphatic group that is used in a reaction described herein includes a reactive end to facilitate conjugation of the aliphatic group with a compound. The reactive end can include, but is not limited to, an aldehyde group (—COH).

The term "alkyl group" means a saturated linear or branched hydrocarbon group including, for example, methyl, ethyl, isopropyl, t-butyl, heptyl, dodecyl, octadecyl, amyl, 2-ethylhexyl, and the like.

The term "alkenyl group" means an unsaturated, linear or branched hydrocarbon group with one or more carbon-carbon double bonds.

The term "alkynyl group" means an unsaturated, linear or branched hydrocarbon group with one or more carbon-carbon triple bonds.

The term "cyclic group" means a closed ring hydrocarbon group that is classified as an alicyclic group, aromatic group, or heterocyclic group.

The term "alicyclic group" means a cyclic hydrocarbon group having properties resembling those of aliphatic groups.

The term "aromatic group" or "aryl group" means a mono- or polynuclear aromatic hydrocarbon group.

The term "heterocyclic group" means a closed ring hydrocarbon in which one or more of the atoms in the ring is an element other than carbon (e.g., nitrogen, oxygen, sulfur, etc.). A group that may be the same or different is referred to as being "independently" something.

The term "sphingolipid" means a class of aliphatic amino alcohols that include the structure sphingosine. Examples of simple sphingolipids include, but are not limited to, ceramides. Examples of ceramides include, but are not limited to, dihydroceramide, ceramide, and phytoceramide. Examples of complex sphingolipids include, but are not limited to, sphingomyelins and glycosphingolipids.

The term "glycolipid" means a compound that includes a lipid and a glycan. Lipids include, but are not limited to, aliphatic groups that are soluble in a nonpolar solvent. Examples of glycolipids include, but are not limited to, glycosphingolipids. Examples of glycosphingolipids include, but are not limited to, cerebrosides, gangliosides, globosides, glycophosphosphingolipids, and sphigomyelins. Examples of cerebrosides include galactocerebrosides, glucocerebrosides, and sulfatides. Examples of gangliosides include, but are not limited to, GM1, GM2, and GM3.

The term "glycan" means the carbohydrate component of a compound. A glycan may contain one monosaccharide, or it may contain two or more monosaccharides linked by glycosidic bonds. A glycan can include nonrepeating or repeating monosaccharides, or both. As used herein, the term "glycan" is interchangeable with the term saccharide, which includes a monosaccharide, a disaccharide, a trisaccharide, etc.; it can include an oligosaccharide or a polysaccharide. An oligosaccharide is an oligomeric saccharide that contains two or more saccharides. The structure of an oligosaccharide is typically characterized by a particular identity, order, linkage positions (including branch points), and linkage stereochemistry ($\alpha$, $\beta$) of the monomers, and as a result has a defined molecular weight and composition. In a polysaccharide, the identity, order, linkage positions (including branch points) and/or linkage stereochemistry can vary from molecule to molecule. A glycan can be branched or unbranched. A complex glycan is a glycan that contains at least one branch point. In a complex or branched glycan, the monosaccharide at the branch point is covalently linked to two other saccharides at carbons other than C1. For example, a branch point monosaccharide may be linked to other monosaccharides at C4 and C6, in addition to being linked to another monosaccharide or to an amino acid at C1. A complex glycan may be, without limitation, biantennary, triantennary, or tetraantennary. A glycan that is used in a reaction described herein includes a reducing end to facilitate conjugation of the glycan with a compound. The reducing end can include an anomeric leaving group such as trichloroacetimidate —C(NH)—CCl$_3$, phenyltrifluoroacetimidate —C(NPh)-CF$_3$, trifluoroacetimidate —C(NH)—CF$_3$; thioformimidate, thioalkyl, thiophenyl, or S-glycosyl N-phenyltrifluoroacetimidate.

The term "glycosylation" refers to the covalent attachment of at least one glycan moiety to a molecule, e.g., a sphingosine or another glycan, by a glycosydic linkage. The term "glycosylation" as used herein should be broadly construed so as to encompass the covalent linkage of any glycan moieties to a lipid-containing compound such as, but not limited to, a sphingosine or a ceramide.

The term "glycosidic linkage" refers to two characteristics, (i) the position or configuration of the anomeric carbon of a monomer and (ii) the linkage position between the anomeric carbon of the monomer and the carbon bearing the connecting oxygen of the following monomer. The position or configuration of the anomeric carbon is designated alpha ($\alpha$) or beta ($\beta$). In the $\alpha$ anomer, the —OH substituent on the anomeric carbon rests on the opposite side (trans) of the ring from the CH$_2$OH side branch. In the $\beta$ anomer, the —OH substituent on the anomeric carbon rests on the same side (cis) of the plane of the ring as the —CH$_2$OH side branch. In the notation sometimes used herein, the letter "$\alpha$" is used to designate an alpha bond and the letter "$\beta$" is used to designate a beta bond. The anomeric carbon of a carbohydrate monomer can be either carbon C1 or carbon C2.

The enantiomeric excess of a compound of the disclosure can be determined using standard analytical assays such as gas chromatography or HPLC with a column having a chiral stationary phase (CSP). Suitable columns with a CSP are available from Chiral Technologies, Inc., Westchester, PA Enantiomeric excess (% ee) is calculated according to Equation 1.

$$\text{enantiomeric excess (\% ee)} = \frac{(\text{mole \% of major enantiomer}) - (\text{mol \% of minor enantiomer})}{(\text{mole \% of major enantiomer}) + (\text{mole \% of minor enantiomer})} \times 100 \quad \text{Equation 1}$$

Enantiomeric excess (% ee) can be calculated from a chiral HPLC chromatogram by comparing the peak areas of the major enantiomer and minor enantiomer signals according to Equation 2.

$$\text{enantiomeric excess (\% ee)} = \frac{(\text{peak area of major enantiomer}) - (\text{peak area of minor enantiomer})}{(\text{peak area of major enantiomer}) + (\text{peak area of minor enantiomer})} \times 100 \quad \text{Equation 2}$$

In any embodiment of a composition that includes a compound described herein, such as Compound 10, the compound is present in the composition in at least 70% enantiomeric excess, at least 75% enantiomeric excess, at least 80% enantiomeric excess, at least 90% enantiomeric excess, at least 95% enantiomeric excess, at least 96% enantiomeric excess, at least 96% enantiomeric excess, at least 97% enantiomeric excess, at least 98% enantiomeric excess, at least 99% enantiomeric excess, at least 99.5% enantiomeric, or at least 99.8% enantiomeric excess.

In any embodiment of a composition that include a compound described herein, such as Compound 10, the opposite enantiomer to the compound is present in the composition in less than 30%, in less than 25%, in less than 20%, in less than 10%, less than 5%, less than 2.5%, less than 2%, less than 1.5%, less than 1%, less than 0.5%, less than 0.25%, or less than 0.1%.

When a group is present more than once in a formula described herein, each group is "independently" selected, whether specifically stated or not. For example, when more than one Y group is present in a formula, each Y group is independently selected. Furthermore, subgroups contained within these groups are also independently selected. For example, when each Y group contains an R1, each R1 is also independently selected.

The term "and/or" means one or all of the listed elements or a combination of any two or more of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided. The term "consisting of" means including, and limited to, whatever follows the phrase "consisting of." That is, "consisting of" indicates that the listed elements are required or mandatory, and that no other elements may be present. The term "consisting essentially of" indicates that any elements listed after the phrase are included, and that other elements than those listed may be included provided that those elements do not interfere with or contribute to the activity or action specified in the disclosure for the listed elements.

Unless otherwise specified, "a," "an," "the," and "at least one" are used interchangeably and mean one or more than one.

Conditions that are "suitable" for an event to occur, such as a reaction described herein, or "suitable" conditions are conditions that do not prevent such events from occurring. Thus, these conditions permit, enhance, facilitate, and/or are conducive to the event.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

Throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed Subranges Such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The following detailed description of illustrative embodiments of the present disclosure may be best understood when read in conjunction with the following drawings.

DETAILED DESCRIPTION

The present disclosure provides a novel synthesis of D-erythro-sphingosine (Sph). In certain embodiments, D-erythro-sphingosine is prepared at a large, commercially relevant scale, such as on a kilogram scale. The synthesis can include starting from a suitable L-serine ester or starting with any intermediate compound described herein. The disclosure also includes compounds synthesized by the methods described herein, including compounds synthesized as intermediates as well as methods for using intermediates.

Sphingosine is a three-carbon chain with two alcohols and amine attached, and a $—C_{13}H_{27}$ aliphatic group. D-erythro-sphingosine is shown below with the numbering scheme used herein to assist in describing certain steps in the synthesis.

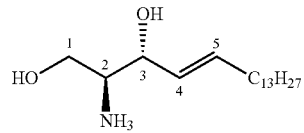

Synthesis of D-erythro-sphingosine and related compounds.

Figure 1:
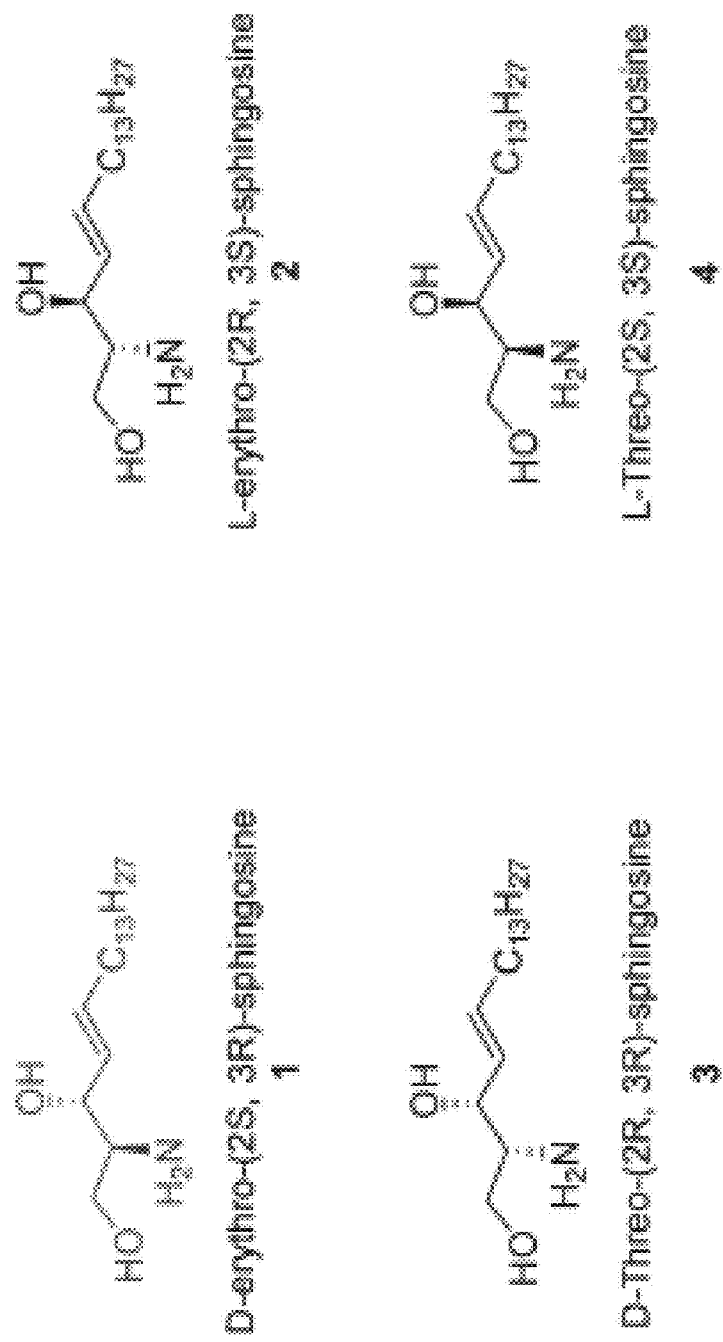
FIG. 1 shows the four stereo isomers of sphingosine.
Figure 2A:
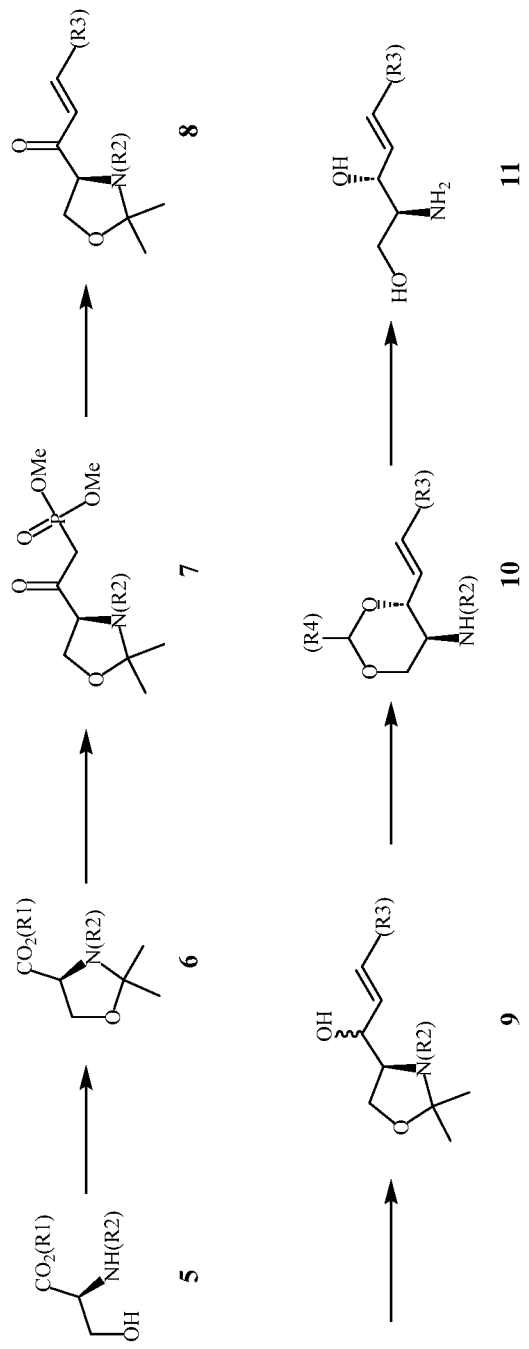
FIG. 2A-2C show Schemes 1 and 2.
Figure 2B:
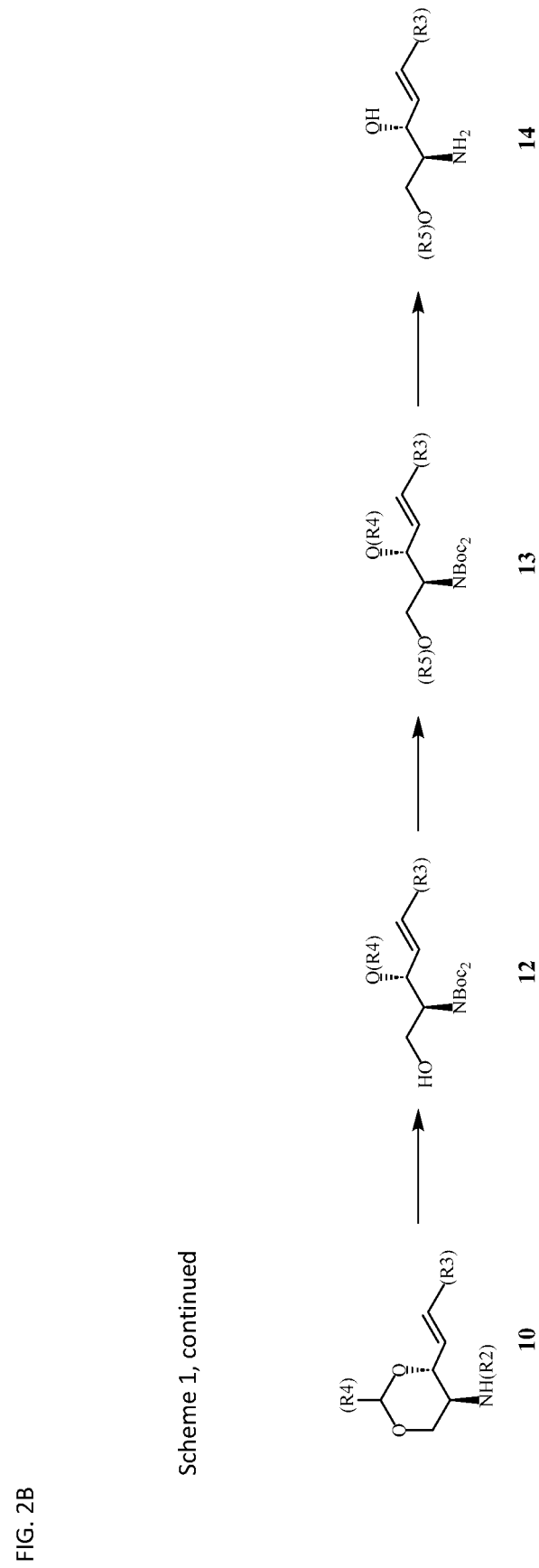

In one embodiment, the stereoselective synthesis of D-erythro-sphingosine can include the steps as shown in Scheme 1 (FIG. 2A-2B). Scheme 1 can also be used to synthesize related compounds by replacing the $—C_{13}H_{27}$ at R3 with other aliphatic groups.

R1 in Scheme 1 is a C1-C5 alkyl group. Representative linear alkyl groups include methyl, ethyl, n-propyl, n-butyl, and n-pentyl. Representative branched alkyl groups include isopropyl, sec-butyl, isobutyl, tert-butyl, isopentyl, neopentyl, 1-methylbutyl, 2-methylbutyl, 3-methylbutyl, 1,1-dimethylpropyl and 1,2-dimethylpropyl. Representative cyclic alkyl groups include cyclopentyl, and cyclopropyl. In one embodiment, R1 is -methyl.

R2 in Scheme 1 is an amine protecting group selected from, but not limited to, benzyloxycarbonyl (Cbz), p-methoxybenzyloxycarbonyl (Moz or MeOZ), tert-Butyloxycarbonyl (Boc), 9-Fluorenylmethyloxycarbonyl (Fmoc), Acetyl (Ac), Benzoyl (Bz), Benzyl (Bn), Carbamate, p-Methoxybenzyl (PMB), 3,4-Dimethoxybenzyl (DMPM), Tosyl (Ts), 2,2,2-Trichloroethoxycarbonyl (Troc), Trifluoroacetamide, Trityl, and other Sulfonamides (Nosyl and Nps).

R3 in Scheme 1 and 2 is an aliphatic group of at least 2, at least 6, or at least 10 carbons and no greater than 36, no greater than 30, no greater than 25, or no greater than 20 carbons. In one embodiment, the aliphatic group is an alkyl group. One linear alkyl group includes, but is not limited to, $C_{13}H_{27}$. In one embodiment, the aliphatic group is an alkenyl group, e.g., the aliphatic group is saturated. Representative alkenyl groups include a linear hydrocarbon group that includes one, two, three, or four carbon-carbon double bonds. In one embodiment, a carbon-carbon double bond can be present at the omega-3, omega-6, or omega-9 position, or combinations thereof, and in combination with one or more carbon-carbon double bonds at other positions within an aliphatic group. Specific examples include the aliphatic groups present on the fatty acids linoleic acid (LA), ω-linolenic acid (ALA), n-3 fatty acids, e.g., eicosapentaenoic acid (EPA) and docosahexaenoic acid (DHA). Unsaturated alkenyl groups can include one or more carbon-carbon double bonds in the trans-orientation, one or more carbon-carbon double bonds in the cis-orientation, or a combination thereof. Specific examples include the aliphatic groups present on the fatty acids oleic acid, elaidic acid, propionic acid, butyric acid, Valeric acid, caproic acid, enanthic acid, caprylic acid, pelargonic acid, capric acid, undecylic acid, lauric acid, tridecylic acid, myristic acid, pentadecylic acid, palmitic acid, margaric acid, Stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, henatriacontylic acid, myristoleic acid, palmitoleic acid, sapienic acid, oleic acid, elaidic acid, vaccenic acid, linoelaidic acid, α-linolenic acid, and erucic acid. The use of $C_{13}H_{27}$ in the R3 position results in the synthesis of D-erythro-sphingosine.

R4 in Scheme 1 and 2 is a hydrogen or a hydroxyl protecting group selected from, but not limited to, Methyl, t-butylmethyl, t-butyl ethyl, phenylethyl, 2-(methoxycarbonyl)ethylidene (Mocdene), 2-(t-butylcarbonyl)ethylidene (Bocdene), 2-phenylsulfonylethylidene (PSE), 2,2,2-trichloroethylidene, 3-(benzyloxy) propyl, Acrolein, isopropylidene, cyclopentylidene, cyclohexylidene, cycloheptylidene, 1-(4-methoxyphenyl)ethylidene, 2,4-dimethoxybenzylidene, 3,4-diemethoxybenzylidene, p-acetoxybenzylidene, 4-(t-butyldimethylsilyloxy)benzylidene, 2-nitrobenzylidene, 4-nitrobenzylidene, mesitylene, 6-bromo-7-hydroxycoumarin-2-yl-methylidene, 1-naphthaldehye, 2-naphthaldehye, 9-anthracene, benzophenone, di-(p-anisyl)methyliene, xanthen-9-ylidene, 2,7-dimethylxanthen-9-ylidene, Acetyl (Ac), Benzoyl (Bz), Benzyl (Bn), β-Methoxyethoxymethyl (MEM), Dimethoxytrityl, (DMT), Methoxymethyl (MOM), Methoxytrityl (MMT), p-Methoxybenzyl (PMB), p-Methoxyphenyl ether (PMP), Methylthiomethyl, Pivaloyl (Pv), Tetrahydropyranyl (THP), Tetrahydrofuranyl (THF), Trityl (triphenylmethyl, Tr), Silyl ethers such as trimethylsilyl (TMS), tert-butyldimethylsilyl (TBDMS), tri-iso-propylsilyloxymethyl (TOM), and triisopropylsilyl (TIPS) ethers), 1,3-(1,1,3,3-tetraisopropyldisiloxanylidene), 1,1,3,3-tetra-t-butoxydisiloxanylidene, o-xylyl, Methyl ethers, and Ethoxyethyl ethers (EE).

R5 in Scheme 1 is a glycan, phosphorylethanolamine, or phosphorylcholine.

R6, R7, R8, R9, R10, R11, and R12 in Scheme 2 are each independently an oxygen protecting group selected from, but not limited to, Acetyl (Ac), Benzoyl (Bz), Benzyl (Bn), β-Methoxyethoxymethyl (MEM), Dimethoxytrityl, (DMT), Methoxymethyl (MOM), Methoxytrityl (MMT), p-Methoxybenzyl (PMB), p-Methoxyphenyl (PMP), Methylthiomethyl, Pivaloyl (Pv), Tetrahydropyranyl (THP), Tetrahydrofuranyl (THF), Trityl (triphenylmethyl, Tr), Silyl ethers such as trimethylsilyl (TMS), tert-butyldimethylsilyl (TBDMS), tri-iso-propylsilyloxymethyl (TOM), and triisopropylsilyl (TIPS) ethers), Methyl ethers, and Ethoxyethyl ethers (EE).

Scheme 1 (FIG. 2A) includes reacting Compound 5 to protect the primary alcohol and the secondary amine as the acetonide to obtain Compound 6 (see U.S. Pat. No. 9,708,354).

The protected L-serine derivative Compound 5 can be produced using routine methods or can be purchased. The primary alcohol and the secondary amine of Compound 5 are protected to result in the acetonide. For instance, a protecting group such as tert-Butyloxycarbonyl (Boc) can be used with 2,2-dimethoxypropane in the presence of $BF_3·Et_2O$ to provide the acetonide Compound 6. The skilled person will recognize that other protecting groups can be used and compounds other than 2,2-dimethoxypropane and $BF_3·Et_2O$ can be used. For instance, acetone in the presence of an acid can be used.

Compound 6 can be reacted with phosphonate to yield Compound 7 (see U.S. Pat. No. 9,708,354).

In one embodiment, Compound 6 can be by transformed into the corresponding β-ketophosphonate 7 by treatment with an excess amount of lithium dimethyl methylphosphonate at a temperature of −70 to −80° C. Optionally, in order to limit purification steps and use an economical and efficient approach, Compound 6 can be used directly with no purification.

Compound 7 can be reacted with an aliphatic group to result in Compound 8 (see U.S. Pat. No. 9,708,354).

In order to achieve the desired E-configuration between C4 and C5 a reaction such as the Horner-Wadsworth-Emmons reaction can be used (Wadsworth, Synthetic Applications of Phosphoryl-Stabilized Anions. In *Organic Reactions*, 1977, pp 73-253). In one embodiment, the β-ketophosphonate Compound 7 can be reacted with an aliphatic group, such as myristyl aldehyde, in the presence of $K_2CO_3$ in an organic solvent such as $CH_3CN$ with water to form exclusively the E-olefin derivative Compound 8 in good yield (55% over three steps). Optionally, column purification can be used to increase the diastereomeric excess of the product in the next reaction. Methods for column purification are known to the skilled person, and include, but are not limited to, silica gel chromatography.

A diastereoselective reaction can be performed on Compound 8 to yield a mixture of the D-erythro and L-threo isomers of Compound 9 (see U.S. Pat. No. 9,708,354). In one embodiment, a Luche reduction with $CeCl_3/NaBH_4$ can be used to give a mixture of R and S diastereomers 9 with the desired R isomer as the major product (9:1 R/S).

Known methods typically deprotect Compound 9 to form a mixture of diastereomers, including the protected D-erythro isomer; however, purifying the diastereomers is difficult. For instance, when R3 is —$C_{13}H_{27}$ the protected D-erythro isomer is D-erythro-sphingosine, and many methods for producing D-erythro-sphingosine use inefficient chromatographic methods for purification of the diastereomers. In a large-scale synthesis these purification approaches are laborious and often give a mixture due to the free bond rotation around C2 and C3. The inventors addressed this problem by developing a more reliable and straightforward large-scale approach to purify the diastereomers. Cyclic structures encompassing the chiral centers were formed by simultaneously protecting the diols as an acetal, thereby locking the free bond rotation around C2 and C3 and making the separation easier. In one embodiment, deprotection of the oxazolidine moiety in compound 9 diastereomers using p-TsOH/MeOH followed by forming a six-membered ring acetal using anisaldehyde dimethyl acetal in presence of camphorsulfonic acid or p-toulenesulfonic acid in a solvent such as dichloromethane, DMF, or acetonitrile, led to a mixture of the diastereomeric acetals that could be cleanly separated as observed by thin-layer chromatography. As an alternative to anisaldehyde dimethyl acetal, either anisaldehyde ethyl acetal, anisaldehyde propyl acetal, or anisaldehyde iso butyl acetal can be used.

Accordingly, in one embodiment the method includes reacting Compound 9 under conditions to deprotect the oxazolidine moiety and then form a six-membered dioxane ring that prevents free bond rotation around C2 and C3. The result is a mixture of diastereomers, including the protected D-erythro isomer (Compound 10).

In one embodiment, the protected D-erythro isomer (Compound 10) can be separated from the mixture of protected the D-erythro and L-threo diastereomers. The acetal protected D-erytho isomer can be crystallized out from the mixture of D-erythro and L-threo diastereomers in 20% hexane/EtOAc. Astonishingly, when R3 was —$C_{13}H_{27}$, purification yielded the enantiomeric excess of compound 10 (78%), thus making the synthetic route more applicable for a large-scale synthesis of sphingosine and related compounds. Other methods for purification can be used, such as silica gel chromatography; however, in some embodiments crystallization is preferred.

Compound 10 can be deprotected to yield Compound 11. When R3 is —$C_{13}H_{27}$, the result of deprotecting Compound 10 is D-erythro-sphingosine (Compound 1).

Methods for global deprotection of compound 10 depend on the protection groups present and are known to the skilled person.

Alternatively, instead of being subjected to conditions for global deprotection, Compound 10 can be converted to an acceptor compound that can be used for the synthesis of other compounds. Thus, the present disclosure includes converting compound 10 to a protected compound 12 (Scheme 1, FIG. 2B. The conversion of Compound 10 to Compound 12 includes replacing the protecting group at R2 with an amine protecting group such as Troc, Fmoc, Acetyl, phthalimides, TFA, Bn, Cbz, Ts, or Boc, followed by reductive opening of the 6-membered dioxane ring. In one embodiment, when R4 is p-methoxybenzylidene acetal a selective reductive opening can be achieved with $AlH_3$. In one embodiment, the amine protecting group is Boc. The skilled person will recognize that the steps useful in replacing the protecting group at R2 with an amine protecting group such as Troc, Fmoc, Acetyl, phthalimides, TFA, Bn, Cbz, Ts, or Boc will depend on which protecting group is present at R2. For instance, when R2 is Boc the replacing can occur by reacting with $Boc_2O$ in the presence of triethylamine in acetonitrile.

Also provided by the present disclosure is a method for using Compound 12 to produce sphingosines and glycolipids such as glycosphingolipids (GSLs). In one embodiment, the method includes glycosylation of Compound 12 with a glycan to result in Compound 13. Deprotection of Compound 13 yields a glycolipid Compound 14. Compound 13 can be used in additional reactions to add other glycans to the glycan of Compound 13 using enzymatic or chemoenzymatic methods known to the skilled person. The method is not intended to be limited by the identity of the glycan or glycans added to Compound 12.

Figure 2C:
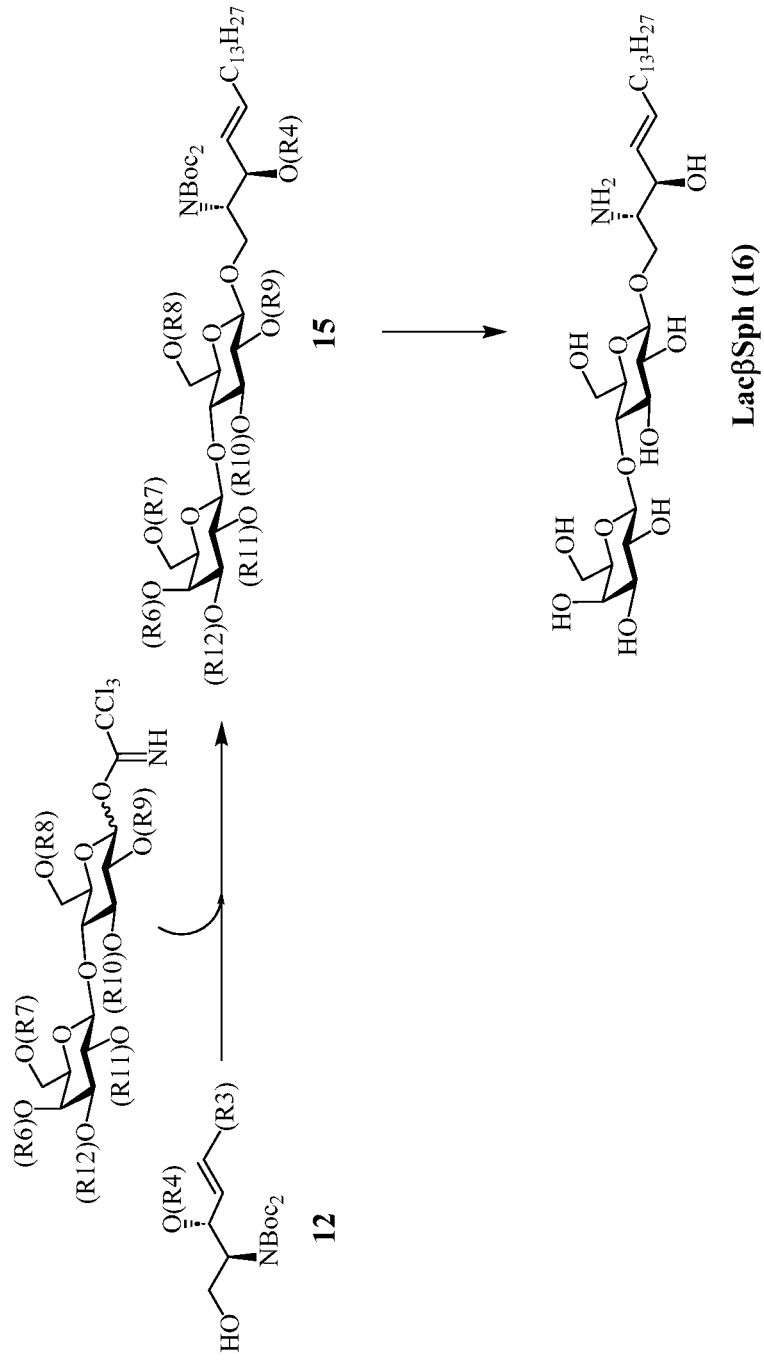

In one embodiment as disclosed in Scheme 2 (FIG. 2C), when the glycan is lactose and R3 of Compound 12 is —$C_{13}H_{27}$ the resulting product is Compound 15, a protected precursor to Lactosyl Sphingosine (Compound 16). Lactosyl Sphingosine (LacβSph) is recognized as the common and initial precursor needed for the synthesis of sphingolipids and GSLs (Yu et al., Org Biomol Chem 2018, 16 (22), 4076-4080). Thus, Compound 12 is a useful intermediate in the synthesis of LacβSph and the synthesis of other GSL products. Lactosyl Sphingosine can be further modified in multiple ways. For instance, LacβSph can be further modified to include an aliphatic group at the amine.

In one embodiment, Compound 12 can be modified using routine methods to include an aliphatic group at the amine to result in a ceramide. The skilled person will recognize that a ceramide can then be further modified to result in many different sphingolipids including, but not limited to, a simple sphingolipid or a complex sphingolipid.

The invention is defined in the claims. However, below there is provided a non-exhaustive listing of non-limiting exemplary aspects. Any one or more of the features of these aspects may be combined with any one or more features of another example, embodiment, or aspect described herein.

Exemplary Aspects

Aspect 1 is a compound of the following structure:

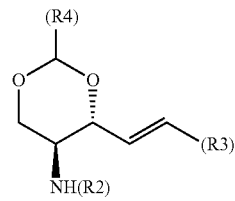

10 wherein R2 and R4 are each independently a protecting group, and wherein R3 is an aliphatic group of at least 2 to no greater than 36 carbons.

Aspect 2 is the compound of Aspect 1, wherein R2 is tert-Butyloxycarbonyl (Boc).

Aspect 3 is the compound of Aspect 1 or 2, wherein R4 is p-Methoxybenzyl (PMB).

Aspect 4 is the compound of any one of Aspects 1-3, wherein R3 is $C_{13}H_{27}$.

Aspect 5 is a compound of the following structure:

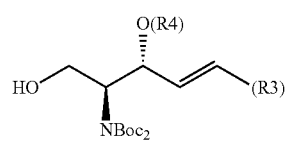

12 wherein R3 is an aliphatic group of at least 2 to no greater than 36 carbons, and wherein R4 is a protecting group.

Aspect 6 is the compound of Aspect 5, wherein R4 is PMB.

Aspect 7 is the compound of Aspect 5 or 6, wherein R3 is $C_{13}H_{27}$.

Aspect 8 is a compound of the following structure:

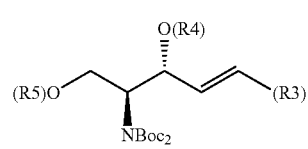

13 wherein R3 is an aliphatic group of at least 2 to no greater than 36 carbons, wherein R4 is a protecting group, and wherein R5 is a glycan, phosphorylethanolamine, or phosphorylcholine.

Aspect 9 is the compound of Aspect 8, wherein R3 is $C_{13}H_{27}$.

Aspect 10 is the compound of Aspect 8 or 9, wherein R4 is PMB.

Aspect 11 is the compound of any one of Aspects 8-10, wherein R5 has the following structure:

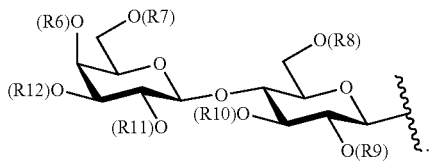

Aspect 12 is the compound of Aspect 11, wherein R5, R6, R7, R8, R9, R10, R11, and R12 are each independently a protecting group.

Aspect 13 is the compound of Aspect 11 or 12, wherein R5, R6, R7, R8, R9, R10, R11, and R12 are each Bz.

Aspect 14 is the compound of any one of Aspects 11-13, wherein the compound has the following structure:

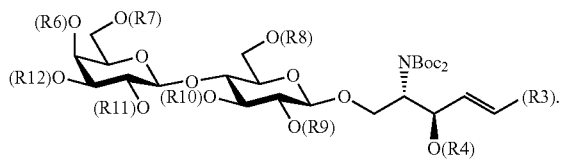

Aspect 15 is a composition comprising of a mixture of D-erythro and L-threo isomers having the following structure:

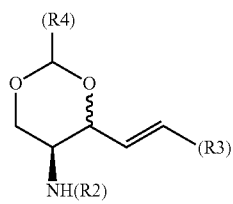

wherein R2 is a protecting group, wherein R3 is an aliphatic group of at least 2 to no greater than 36 carbons, and wherein R4 is a protecting group, and wherein the D-erythro isomer having the following structure:

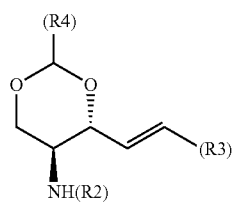

is present in the composition in at least 70% enantiomeric excess.

Aspect 16 is a method for synthesizing D-erythro-sphingosine, comprising:

(a) reacting a first mixture of diastereomers having the following structure:

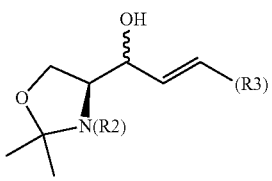

wherein R2 is a protecting group, wherein R3 is C13H27, and wherein the reacting comprises conditions suitable for formation of a mixture of D-erythro and L-threo isomers having the following structure:

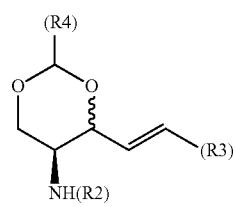

wherein R4 is a protecting group, (b) purifying the protected D-erythro isomer from the mixture of protected D-erythro and protected L-threo isomers, and (c) deprotecting the protected D-erythro isomer to result in D-erythro-sphingosine.

Aspect 17 is the method of Aspect 16, wherein the purifying comprises crystallization.

Aspect 18 is a method for synthesizing an acceptor compound, comprising:

(a) reacting a protected D-erythro compound comprising a 6-membered heterocyclic ring and having the following structure:

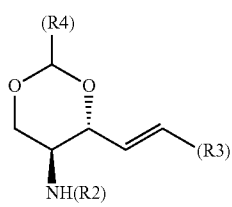

wherein R2 and R4 are each independently a protecting group, and wherein R3 is an aliphatic group of at least 2 to no greater than 36 carbons, wherein the reacting comprises conditions suitable for converting R2 to Boc₂, and (b) opening the 6-membered heterocyclic ring to result in an acceptor compound having the following structure:

12

[Structure: HO-CH2-CH(NBoc2)-CH(O(R4))-CH=CH-(R3)]

Aspect 19 is the method of Aspect 18, wherein R3 is C13H27.

Aspect 20 is the method of Aspect 18 or 19, wherein R4 is PMB.

Aspect 21 is a method for synthesizing a compound comprising a 6-membered heterocyclic ring and having the following formula:

[Structure: 1,3-dioxane with (R4) at C2, NH(R2) substituent, and vinyl-(R3) substituent]

wherein R2 and R4 are each independently a protecting group, and wherein R3 is an aliphatic group of at least 2 to no greater than 36 carbons, the method comprising reacting a compound of the following formula:

9

[Structure: oxazolidine with OH and CH=CH-(R3) substituent, N(R2)]

wherein the reacting comprises a deprotecting step followed by forming the 6-membered heterocyclic ring to prevent free bond rotation around C2 and C3.

Aspect 22 is the method of Aspect 21, wherein R3 is $C_{13}H_{27}$.

Aspect 23 is the method of Aspect 21 or 22, wherein R4 is PMB.

Aspect 24 is a method for making a glycolipid comprising:

providing a compound of the following structure:

12

[Structure: HO-CH2-CH(NBoc2)-CH(O(R4))-CH=CH-(R3)]

wherein R4 is a protecting group, and wherein R3 is an aliphatic group of at least 2 to no greater than 36 carbons, and glycosylating the compound by linking a glycan comprising a reducing end to the free hydroxyl of the compound to yield a protected glycolipid having the following structure:

13

[Structure: (R5)O-CH2-CH(NBoc2)-CH(O(R4))-CH=CH-(R3)]

wherein R5 is the glycan.

Aspect 25 is the method of Aspect 24, further comprising deprotecting the protected glycolipid.

Aspect 26 is the method of Aspect 24 or 25, wherein R3 is C13H27.

Aspect 27 is the method of any one of Aspects 24-26, wherein R4 is PMB.

Aspect 28 is the method of any one of Aspects 24-27, wherein R5 is lactose.

Aspect 29 is a method for making lactosyl β-sphingosine, comprising deprotecting a compound of the following structure:

15

[Structure: lactose-linked sphingosine derivative with protecting groups R6-R12 and NBoc2, C13H27 chain]

wherein R4, R5, R6, R7, R8, R9, R10, R11, and R12 are each independently a protecting group.

EXAMPLES

The present disclosure is illustrated by the following examples. It is to be understood that the particular examples, materials, amounts, and procedures are to be interpreted broadly in accordance with the scope and spirit of the disclosure as set forth herein.

Example 1

Economic Chemical Synthesis of Sphingosine and Lactosylsphingosine

Gangliosides are sialic acid-containing glycosphingolipids that have been found in the cell membranes of all vertebrates. Both the glycan and the ceramide lipid components contribute to their important biological functions. GM3 is a major ganglioside and a precursor for many other more complex gangliosides. To obtain structurally diverse GM3 gangliosides containing various sialic acid forms and different fatty acyl chains in low cost, lactosyl sphingosine was chemically synthesized from an inexpensive L-serine derivative (Yu et al., J. Org. Chem. 2021, 86, 8672-8682).

Introduction

Gangliosides are sialic acid-containing glycosphingolipids (GSLs). They have been found in the cell plasma membranes of all vertebrates and are the most abundant in their central nervous systems. (1) Similar to other GSLs, gangliosides are structurally diverse with differences in both the glycan and the lipid components. Compared to other GSLs, gangliosides have additional structural variations on the sialic acid forms. In addition to N-acetylneuraminic acid (Neu5Ac), which is the most common sialic acid form, 9-O-acetyl Neu5Ac (Neu5,9Ac2), (2) 7-O-acetyl Neu5Ac (Neu5,7Ac2), (3) and nonhuman sialic acid N-glycolyl-neuraminic acid (Neu5Gc) (4,5) have been found in gangliosides. Ceramide, the unique lipid component of GSLs including gangliosides, consists of a sphingoid base and a single acyl chain. (6) In mammals, a sphingosine with 18 or 20 carbons (7) is the most common sphingoid base, while the fatty acyl component varies significantly in lengths and degrees of unsaturation (16:0 to 26:0/26:1(8) or longer (6)) and with or without additional hydroxylation. (9) The combinations of different ceramides, the glycan structures, and sialic acid forms result in a significantly large number of structurally diverse gangliosides.

GM3 is a major ganglioside and the precursor for the formation of other more complex major ganglio-series gangliosides. (10) Overexpression of GM3 has been connected to cancer, (11,12) and GM3 is among the four gangliosides in a 75-prioritized-cancer-antigen list. (11) The levels of human serum GM3 gangliosides containing various acyl chains have been shown to correlate with risk factors for metabolic diseases. (9) Increased GM3 synthesis has been shown to associate with insulin resistance and impaired wound healing in patients with type 2 diabetes or in related mouse models. (13-15) GM3 has also been shown to inhibit the activities of receptor tyrosine kinases such as the epidermal growth factor receptor, (16-18) and such activity varies according to the sialic acid forms (Neu5Ac or Neu5Gc). (19) GM3 containing the Neu5Gc sialic acid form (Neu5Gc-GM3) has been found in different cancers, (20) and Neu5Gc-GM3 extracted from horse erythrocytes has been used to form very-small-size-proteoliposomes with the Neisseria meningitidis outer membrane protein complex(21) in clinical trials for breast cancer patients. (21-26) Due to the influence of both sialic acid forms and the ceramide structures on the functions of GM3, developing efficient methods for synthesizing structurally diverse GM3 gangliosides is urgently needed. We developed an efficient chemical synthetic process for synthesizing LacβSph from less expensive starting materials. LacβSph can be used as a substrate for the production of GM3 sphingosine and other compounds.

Results and Discussion

Figure 3:
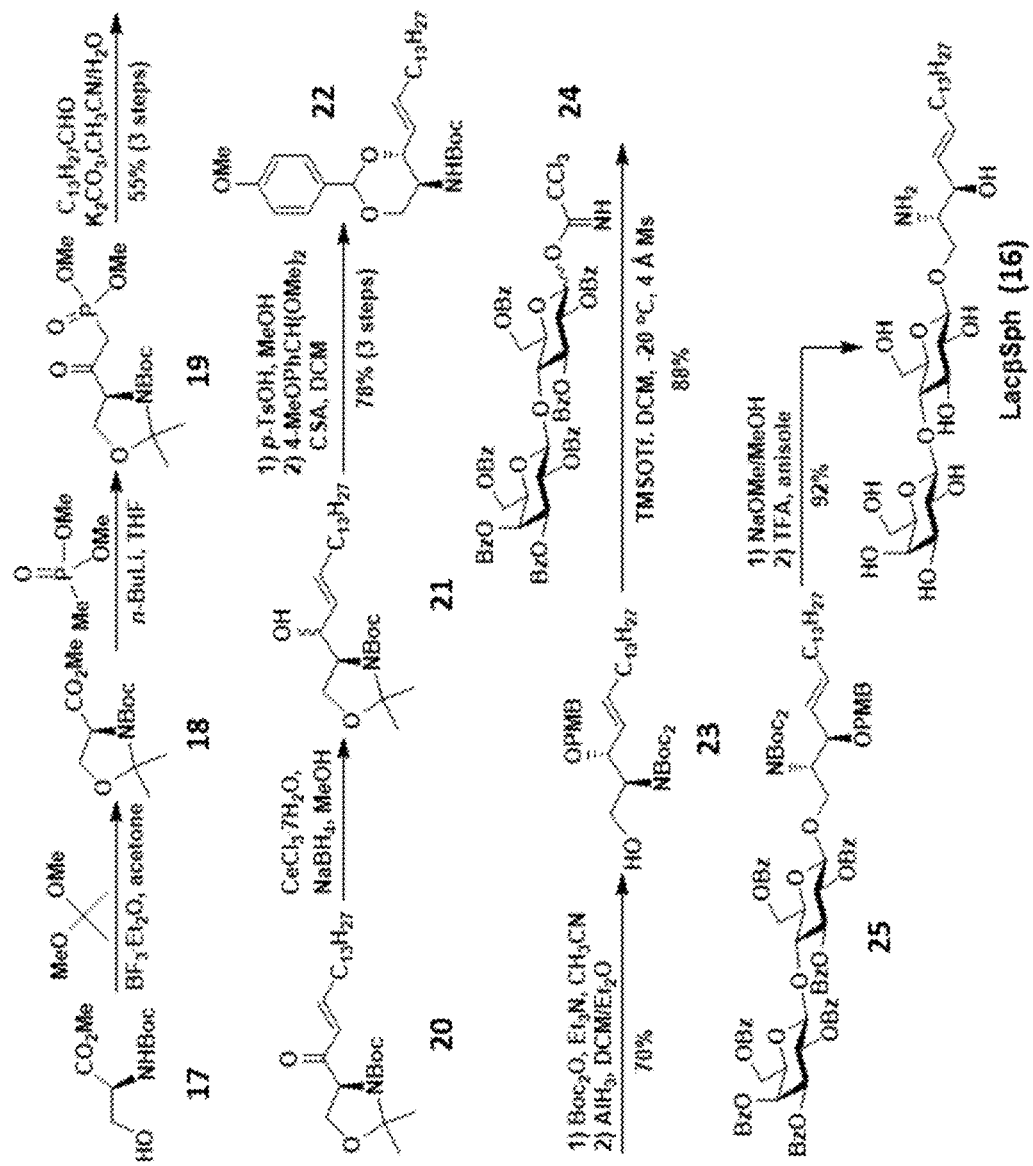
FIG. 3 shows Scheme 3, an example of a chemical synthesis of LacβSph (16) from N-Boc L-serine methyl ester (17) with purification of the desired D-erythro isomer 22 by crystallization.

Efficient chemical synthesis of lactosyl sphingosine (LacβSph) from inexpensive N-Boc L-serine methyl ester. Obtaining LacβSph in large scales is an essential step for one-pot multienzyme chemoenzymatic total synthesis of GM3. Previously, we used commercially available phytosphingosine(27, 28) as a starting material. In order to further decrease the cost to access the critical intermediate LacβSph in large scales more economically, N-Boc L-serine methyl ester 17(29) (Scheme 3, FIG. 3), a compound that is much less expensive than phytosphingosine, was identified as a well-suited starting material.

Figure 4:
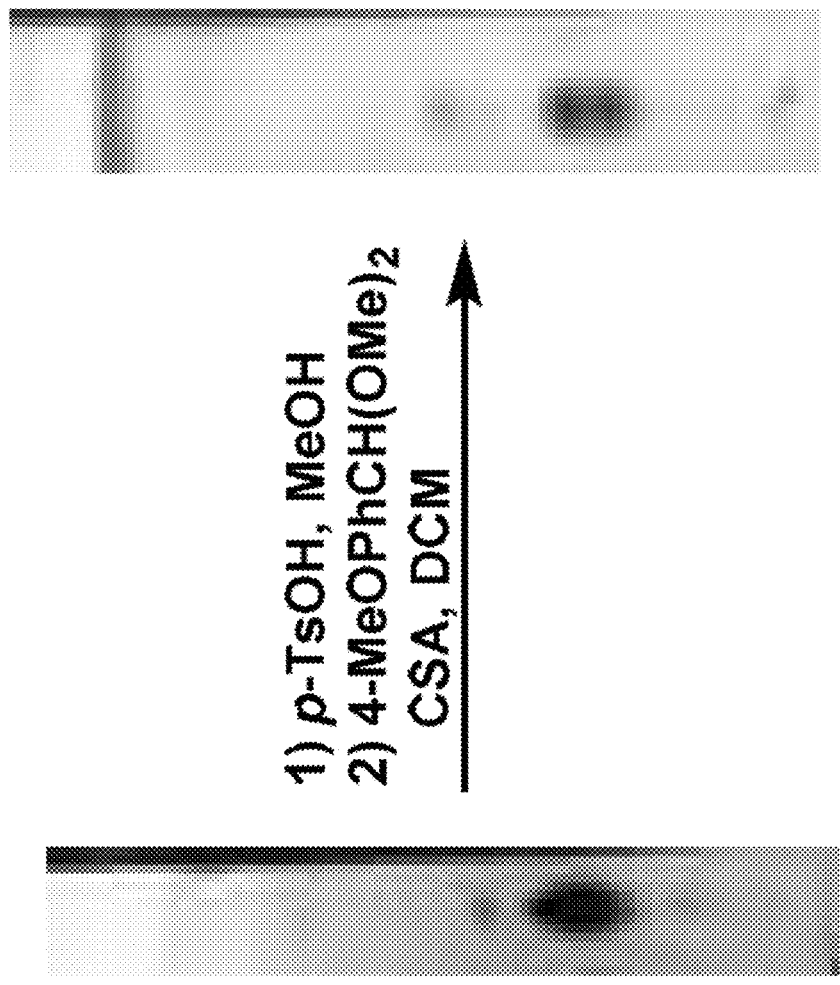
FIG. 4 shows TLC images of the separation of isomers by converting compound 21 to 22.

As shown in Scheme 3 (FIG. 3), the acetonide protection of N(Boc)-protected amino alcohol 17 using 2,2-dimethoxypropane in the presence of $BF_3 \cdot Et_2O$ provided acetonide 18. The purification steps were limited to develop an economical and efficient approach towards the synthesis of LacβSph. Therefore, compound 18 was used directly for the next step by transforming into the corresponding β-ketophosphonate 19 by treatment with an excess amount of lithium dimethyl methylphosphonate at −78° C. The useful step to establish the E olefin geometry in the sphingoid base skeleton was achieved using the Horner-Wadsworth-Emmons reaction. The β-ketophosphonate 19 was reacted with myristyl aldehyde in the presence of $K_2CO_3$ in $CH_3CN/H_2O$ to form exclusively the E-olefin derivative 20 (Koolath et al., Chirality 2020, 32, 308-313) in good yield (55% over three steps). It was then helpful to carry out column purification at this stage to increase the diastereomeric excess of the product in the next reaction the overall final yield. Subsequently, compound 20 was subjected to diastereoselective Luche reduction with $CeCl_3/NaBH_4$ to give a mixture of R and S diastereomers 21 with the desired R isomer as the major product (9:1 R/S). It is worth noting that many of the previous methods reported the use of chromatographic purification of the diastereomers. Such a purification approach in a large-scale synthesis is laborious and would often give a mixture due to the free C—C bond rotation, and so, a more reliable and straightforward large-scale approach to completely purify the diastereomers is necessary. (30-32) In this context, we aimed to develop a more efficient purification strategy. It was rationalized that the open-chain forms of compound 21 diastereomers are conformationally more flexible and are more difficult to separate. (33) In contrast, forming cyclic structures encompassing the chiral centers by simultaneously protecting the diols as an acetal would make the separation easier. Indeed, deprotection of the oxazolidine moiety in compound 21 diastereomers using p-TsOH/MeOH followed by the formation of a six-membered ring acetal using anisaldehyde dimethyl acetal led to a clean separation of the isomers observed by thin-layer chromatography (FIG. 4). Astonishingly, the acetal protected desired D-erythro isomer was readily crystallized out from the mixture in hexane/EtOAc to provide the enantiomerically pure compound 22 (78%), thus making the synthetic route more applicable for a large-scale synthesis of sphingosine. Later, compound 22 was converted to a diBoc-protected sphingosine 23 in good yield (70%) by reacting with $Boc_2O$, followed by selective reductive opening of p-methoxybenzylidene acetal with AlH3. Compound 23 served as a novel acceptor for glycosylation, which was coupled with lactosyl trifluoroacetimidate 24(34) using catalytic TMSOTf as the promoter gave the β-linked product 25 in an excellent yield (88%). Subsequent global deprotection produced LacβSph 16 (92%) on 5.2 grams scale, which can serve as the acceptor substrate for enzymatic synthesis of GM3 glycosphingosines and their derivatives.

Conclusions

In conclusion, an improved process which requires minimal column purification steps for large-scale chemical synthesis of LacβSph from the inexpensive L-serine derivative has been developed. Importantly, D-erythro and D-threo sphingosine derivatives were separated cleanly by forming six-membered acetals, followed by recrystallization of the desired isomer from the mixture, which made the process more reliable and more adaptable for large-scale synthesis. The sphingosine hydrophobic tag in water-soluble LacβSph facilitates the product purification from the enzymatic reaction mixture by using a simple C18-cartridge purification process.

Materials and General Methods

Chemicals were purchased and used without further purification. $^1$H NMR (800 MHz) and $^{13}$C NMR (200 MHz) spectra were recorded on a Bruker AVANCE-800 NMR spectrometer, and $^1$H NMR (600 MHz) and $^{13}$C NMR (150 MHz) spectra were recorded on a Bruker AVANCE-III HD 600 NMR spectrometer. High-resolution electrospray ionization (ESI) mass spectra were recorded using a Thermo Electron LTQ-Orbitrap Hybrid Mass Spectrometer or a Thermo Scientific Q Exactive HF Orbitrap Mass Spectrometer at the Mass Spectrometry Facilities in the University of California, Davis. Silica gel 60 Å (230-400 mesh, Sorbent Technologies) was used for flash column chromatography. Thin-layer chromatography (TLC, Sorbent Technologies) was performed on silica gel plates using anisaldehyde sugar stain for detection. The melting point was recorded on a Stuart SMP10 instrument.

Chemical Synthesis of Lactosyl Sphingosine (16)

3-(tert-Butyl) 4-Methyl (S)-2,2-Dimethyloxazolidine-3,4-dicarboxylate (18)

To the commercially available methyl(tert-butoxycarbonyl)-L-serinate 17 (43 g, 196.1 mmol) in acetone (300 mL) at room temperature (rt), 2,2-dimethoxypropane (217.2 mL, 1.77 mol) was added. To the above reaction mixture, $BF_3 \cdot OEt_2$ (1.40 mL, 11.2 mmol) was added at the same temperature and stirred for 6 h. The reaction mixture was concentrated under reduced pressure and dissolved in dichloromethane (100 mL) and was washed with sat. aq. $NaHCO_3$ solution (500 mL), brine (500 mL), and water (500 mL). The organic layer was dried over anhydrous sodium sulfate, filtered, and concentrated to dryness to obtain compound 18 as a liquid, which was used in the next step without further purification. A small portion of the crude compound was purified using flash column chromatography using hexanes and EtOAc, and the data were in agreement with the reported literature. (35, 36) $^1$H NMR (600 MHz, $CDCl_3$) δ 4.43 (ddd, J=10.1, 6.9, 2.8 Hz, 1H), 4.14 (ddd, J=13.8, 9.2, 7.0 Hz, 1H), 4.04 (ddd, J=15.5, 9.2, 2.8 Hz, 1H), 3.76 (d, J=1.9 Hz, 3H), 1.66 (d, J=19.9 Hz, 3H), 1.52 (d, J=22.4 Hz, 7H), 1.41 (s, 5H).

tert-Butyl (S,E)-4-(Hexadec-2-enoyl)-2,2-dimethyl-oxazolidine-3-carboxylate (20)

To a solution of dimethyl methyl phosphonate in anhydrous THF (150 mL) was added n-BuLi (237.6 mL, 1.6 M in hexanes, 380.6 mmol) slowly over 30 min at −78° C. After stirring for 1 h at the same temperature, crude serine derivative 18 in anhydrous THF (40 mL) was added slowly at the same temperature and stirred for 10 min. The reaction was slowly warmed to 0° C. for a 1 h period, stirred at the same temperature for 30 min, and quenched with the THF/water mixture (5:1, 6 mL) at 0° C. The pH was adjusted to 6.0-7.0 with 20% citric acid and extracted with EtOAc (3×300 mL). The organic layer was dried over anhydrous sodium sulfate, filtered, and concentrated under reduced pressure to obtain crude compound 19, which was used further without purification.

The crude compound 19 and potassium carbonate (54.2 g, 392.2 mmol.) were dissolved in 1 L of acetonitrile. To the above solution, 1-tetradecanal (33.2 g, 156.8 mmol, 0.8 equiv) and 12 mL of water were added to adjust the pH to 9. The reaction was stirred at rt for 12 h. The reaction mixture was filtered, and the solid was washed with 1 L of hexanes. The organic phases were combined and evaporated to dryness under reduced pressure. The crude concentrate was dissolved in 1 L of hexanes and washed with of sat. aq. brine solution (500 L). The organic layer was collected and dried over anhydrous sodium sulfate. The organic layer was filtered, concentrated under reduced pressure, and purified by flash column chromatography using hexanes/EtOAc to obtain 47.2 g (55% yield over three steps) of compound 20, and the data were in agreement with the reported literature. (37) $^1$H NMR (600 MHz, $CDCl_3$) δ 7.0-6.94 (m, 1H), 6.28 (dd, J=27.1, 15.7 Hz, 1H), 4.73-4.48 (m, 1H), 4.21-4.13 (m, 1H), 3.93 (ddd, J=12.8, 9.0, 3.0 Hz, 1H), 2.23 (dt, J=13.5, 6.8 Hz, 2H), 1.68 (d, J=34.2 Hz, 3H), 1.57-1.44 (m, 9H), 1.37 (s, 6H), 1.26 (s, 22H), 0.88 (t, J=7.0 Hz, 3H).

tert-Butyl ((4R,5S)-2-(4-Methoxyphenyl)-4-((E)-pentadec-1-en-1-yl)-1,3-dioxan-5-yl)carbamate (22)

Compound 20 (30 g, 68.6 mmol) and cerium chloride heptahydrate (38.3 g, 102.9 mmol) were stirred in methanol in a 500 mL round-bottom flask over 30 min at rt and cooled to −20° C. A sodium borohydride solution (3.8 g, 102.9 mmol) in 30% caustic soda (15.5 mL) was cooled to 0° C. and then carefully added to the allylic ketone solution dropwise over 2 h. After the complete addition, the reaction was allowed to stir at −20° C. for 30 min and allowed to reach rt over 2 h. Methanol was evaporated at 40° C. under reduced pressure and diluted with $Et_2O$ (300 mL) and filtered. The precipitate was washed with 300 mL of $Et_2O$ over portions, and the organic layer was washed with sat. aq. $NaHCO_3$, dried over anhydrous sodium sulfate, filtered, and concentrated to dryness. The crude compound 21 was used further without purification. The ratio of diastereomers was found to be on an average of 9:1 (D-erythro/L-erythro-sphingosine) using $^1$H crude NMR of 21 and 22.

To the crude solution of compound 21 in anhydrous methanol (300 mL) was added p-TsOH (2.3 g, 13.7 mmol) at 0° C. and allowed to reach rt over 1 h. The reaction mixture was stirred until completion and quenched with sat. aq. $NaHCO_3$ (10 mL). Methanol was evaporated under reduced pressure, and the crude was dissolved in $Et_2O$ (300 mL). The organic layer was washed with water (300 mL), and the organic layer was collected, dried over anhydrous sodium sulfate, and concentrated under reduced pressure to dryness. The crude was dissolved in anhydrous dichloromethane (300 mL). To the reaction mixture, anisaldehyde dimethyl acetal (15.0 g, 82.3 mmol) and camphor sulfonic acid (3.17 g, 13.7 mmol) were added successively at rt. The reaction mixture was stirred over 2 h and quenched with triethylamine (13.7 mmol). The reaction mixture was diluted with dichloromethane (300 mL) and washed with sat. aq. $NaHCO_3$ (300 mL), brine (300 mL), and water (300 mL). The organic layer was dried over anhydrous sodium sulfate and concentrated to dryness under reduced pressure. The D-erythro Isomer was crystallized using 15% hexanes/EtOAc to obtain a pure compound 22 (27.6 g, 78% yield), leaving the other diastereomer in the crude solution. mp 112-114° C. $^1$H NMR (600 MHz, $CD_3OD/CDCl_3$=9:1, by volume) δ 7.38 (d, J=8.4 Hz, 2H, Ar), 6.88 (d, J=9.0 Hz, 2H, Ar), 5.86-5.81 (m, 1H, HC=C), 5.50 (dd, J=7.2, 15.6 Hz, 1H, C=CH), 5.46 (S, 1H, acetal), 4.17-4.14 (m, 1H), 4.02 (t, J=8.4 Hz, 1H, HC—C=C), 3.79 (s, 3H, OMe), 3.62-3.59 (m, 2H), 2.05 (q, J=7.2 Hz, 2H, C=C—$CH_2$), 1.43 (s, 9H), 1.28 (s, 22H), 0.89 (t, J=7.2 Hz, 3H). $^{13}C\{^1H\}$ NMR (150 MHz, $CD_3OD/CDCl_3$=9:1, by volume) δ 161.4, 157.6, 136.8, 131.8, 128.5, 127.9, 114.4, 162.1, 82.9, 70.6, 55.7, 33.3, 32.9, 30.6, 30.5, 30.4, 30.2, 30.1, 30.0, 28.8, 23.5, 14.3. HRMS (ESI-Orbitrap) m/z: [M+Na]$^+$ calcd for $C_{31}H_{51}NNaO_5$ 540.3665; found, 540.3660.

Di-tert-butyl ((2S,3R,E)-1-hydroxy-3-((4-methoxybenzyl)oxy)-octadec-4-en-2-yl)iminodicarbonate (23)

To a solution of compound 22 (20 g, 38.6 mmol) in anhydrous acetonitrile, $Et_3N$ (3.9 g, 38.6 mmol) and $Boc_2O$ (10.1 g, 46.3 mmol) were added successively at rt and stirred over 12 h (0.2 equiv of DMAP was added to increase the rate of the reaction). The solvent was evaporated and dissolved in dichloromethane (500 mL) and washed with 1N HCl (250 mL), sat. aq. NaHCO$_3$ (250 mL), and water (250 mL). The organic layer was dried over anhydrous sodium sulfate, filtered, and concentrated to dryness under reduced pressure. The crude was taken forward without purification.

The crude was co-evaporated with anhydrous toluene (2×50 mL) and dissolved in 1:1 anhydrous Et$_2$O/dichloromethane (200 mL). The reaction mixture was cooled to −20° C., and LiAlH$_4$ (6.6 g, 173.7 mmol) was added. To the above reaction mixture, AlCl$_3$ (4 M in anhydrous Et$_2$O, 7.7 g, 57.9 mmol) was added slowly at −20° C. The reaction mixture was allowed to reach 0° C. and stirred at the same temperature for 3 h. After completion, the reaction mixture was quenched by adding EtOAc (50 mL) and water (50 mL) slowly at 0° C. The reaction mixture was extracted with EtOAc (650 mL) and washed with 1N HCl (350 mL), sat. aq. NaHCO$_3$ (350 mL), and water (350 mL). The organic layer was dried over anhydrous sodium sulfate, filtered, and concentrated to dryness under reduced pressure. The crude was purified using flash column chromatography over silica gel using hexanes/EtOAc to obtain compound 7 (16.7 g, 70% yield). $^1$H NMR (600 MHz, CDCl$_3$) δ 7.22 (d, J=8.5 Hz, 2H, Ar), 6.88 (d, J=8.5 Hz, 2H, Ar), 5.83-5.71 (m, 1H, HC=C), 5.43 (dd, J=15.4, 7.9 Hz, 1H, C=CH), 4.56 (d, J=11.5 Hz, 1H), 4.25 (d, J=11.5 Hz, 1H), 4.00 (s, 1H), 3.95 (d, J=9.4 Hz, 1H), 3.81 (s, 3H, OMe), 3.62 (d, J=6.8 Hz, 2H), 2.89 (s, 1H), 2.10 (dd, J=14.2, 7.0 Hz, 2H, C=C—CH$_2$), 1.44 (s, 9H), 1.28 (s, 21H), 0.90 (t, J=7.0 Hz, 3H). $^{13}$C{$^1$H} NMR (150 MHz, CDCl$_3$) δ 159.2, 155.8, 136.6, 129.9, 129.3, 126.6, 113.8, 81.4, 79.3, 70.1, 62.3, 54.1, 54.8, 32.2, 31.8, 29.6, 29.6, 29.5, 29.4, 29.3, 29.1, 29.0, 28.3, 22.6, 14.0. HRMS (ESIOrbitrap) m/z: [M+H]$^+$ calcd for C$_{36}$H$_{62}$NO$_7$ 620.4526; found, 620.4533.

(2R,3S,4S,5R,6S)-2-((Benzoyloxy)methyl)-6-(((2R, 3R,4S,5R,6R)-4,5-bis(benzoyloxy)-2-((benzoyloxy) methyl)-6-(((2S,3R,E)-2-(bis-(tert-butoxycarbonyl) amino)-3-((4-methoxybenzyl)oxy)octadec-4-en-1-yl) oxy)tetrahydro-2H-pyran-3-yl)oxy)tetrahydro-2H-pyran-3,4,5-triyl Tribenzoate (25)

To a solution of glycosyl donor 24(34) (23.5 g, 19.3 mmol) and acceptor 23 (10 g, 16.13 mmol) in anhydrous dichloromethane was added activated 4 Å MS (25 g) at rt, and the solution was stirred at the same temperature for 2 h. The reaction mixture was cooled to −40° C. using acetonitrile and dry ice. After 10 min, TMSOTf (0.36 mL, 1.6 mmol) was added dropwise at −40° C. The reaction mixture was allowed to stir at the same temperature for 1 h and quenched with triethylamine (400 μL) after confirming the reaction with TLC. The solution was filtrated to remove 4 Å MS, and the filtrate was diluted with dichloromethane (300 mL) and washed with sat. aq. NaHCO$_3$ (200 mL) and brine (200 mL). The organic layer was dried with anhydrous Na$_2$SO$_4$, filtered, and purified over silica gel using hexanes and EtOAc to obtain compound 25 (23.7 g, 88%) as a white foam. $^1$H NMR (600 MHz, CDCl$_3$) δ 8.05-7.99 (m, 10H, Ar), 7.92 (dd, J=8.3, 1.2 Hz, 2H, Ar), 7.75 (dd, J=8.4, 1.2 Hz, 2H, Ar), 7.67-7.63 (m, 1H, Ar), 7.63-7.59 (m, 1H, Ar), 7.59-7.55 (m, 1H, Ar), 7.55-7.49 (m, 5H, Ar), 7.45-7.40 (m, 6H, Ar), 7.40-7.32 (m, 4H, Ar), 7.26-7.22 (m, 2H, Ar), 7.19 (t, J=7.8 Hz, 2H, Ar), 7.13 (d, J=8.6 Hz, 2H, Ar), 6.77 (d, J=8.6 Hz, 2H, Ar), 5.85-5.80 (m, 1H), 5.78-5.72 (m, 2H), 5.48 (dd, J=9.9, 7.9 Hz, 1H), 5.39 (dd, J=10.3, 3.4 Hz, 1H), 5.35 (t, J=6.9 Hz, 1H, HC=C), 5.24 (dd, J=15.4, 8.3 Hz, 1H, C=CH), 4.89 (d, J=7.9 Hz, 1H, anomeric), 4.71 (d, J=7.9 Hz, 1H, anomeric), 4.58 (dd, J=16.0, 5.6 Hz, 2H), 4.53 (dd, J=12.1, 4.3 Hz, 1H), 4.37 (d, J=11.0 Hz, 1H), 4.27 (dd, J=19.5, 10.0 Hz, 2H), 4.20 (d, J=10.9 Hz, 1H), 3.90 (t, J=6.7 Hz, 1H), 3.84-3.81 (m, 1H), 3.79-3.74 (m, 4H), 3.71 (dd, J=11.3, 7.0 Hz, 2H), 3.65 (t, J=8.2 Hz, 1H), 3.56 (dd, J=9.7, 3.0 Hz, 1H), 1.95-1.89 (m, 2H), 1.34 (s, 9H), 1.28 (s, 22H), 0.91 (t, J=7.0 Hz, 3H). $^{13}$C{$^1$H} NMR (150 MHz, CDCl$_3$) δ 165.8, 165.5, 165.4, 165.3, 165.2, 164.8, 159.0, 155.2, 136.7, 133.5, 133.4, 133.3, 133.2, 130.5, 130.0, 129.8, 129.7, 129.6, 129.4, 129.2, 128.8, 128.6, 128.5, 128.5, 128.2, 127.2, 113.6, 101.5, 100.9, 79.2, 79.0, 75.9, 73.0, 72.8, 72.0, 71.8, 71.3, 70.1, 69.8, 68.6, 67.5, 62.5, 61.0, 55.2, 53.1, 32.2, 31.9, 29.7, 29.6, 29.5, 29.3, 29.2, 29.1, 28.3, 22.7, 14.1. HRMS (ESIOrbitrap) m/z: [M+Na]$^+$ calcd for C$_{97}$H$_{109}$NNaO$_{24}$ 1694.7237; found, 1694.7245.

(2S,3R,4S,5R,6R)-2-(((2R,3S,4R,5R,6R)-6-(((2S, 3R,E)-2-Amino-3-hydroxyoctadec-4-en-1-yl)oxy)-4, 5-dihydroxy-2-(hydroxymethyl)-tetrahydro-2H-pyran-3-yl)oxy)-6-(hydroxymethyl)tetrahydro-2Hpyran-3,4,5-triol (16)

To a solution of compound 25 (15 g, 8.9 mmol) in anhydrous methanol (200 mL), NaOMe was added until the pH reached 9. The pH was maintained at 9 over 2 h, and stirring was done at rt over 12 h. The reaction mixture was neutralized with a Dowex 50WX8 acid resin and filtered over Celite. The filtrate was concentrated to dryness under reduced pressure. Hexanes (2×50 mL) were added and decanted to remove the nonpolar side products. The crude was dried under vacuum over 6 h and dissolved in 9:1 TFA/anisole (100 mL) and stirred over 3 h. The solvent was evaporated, and under reduced pressure, the crude was purified using water and acetonitrile over the C18 reverse-phase column to obtain LacβSph 16 (5.2 g, 92%) as a white solid. The data are in agreement with the reported literature. (27)

Citations for Example 1

(1) Yu, R. K.; Nakatani, Y.; Yanagisawa, M. The Role of Glycosphingolipid Metabolism in The Developing Brain. J. Lipid Res. 2009, 50, S440-S445.

(2) Cavdarli, S.; Dewald, J. H.; Yamakawa, N.; Guérardel, Y.; Terme, M.; Le Doussal, J.-M.; Delannoy, P.; Groux-Degroote, S. Identification of 9-O-Acetyl-N-acetyl-neuraminic Acid (Neu5,9Ac2) as Main O-Acetylated Sialic Acid Species of GD2 in Breast Cancer Cells. Glycoconjugate J. 2019, 36, 79-90.

(3) Wipfler, D.; Srinivasan, G. V.; Sadick, H.; Kniep, B.; Arming, S.; Willhauck-Fleckenstein, M.; Vlasak, R.; Schauer, R.; Schwartz-Albiez, R. Differentially Regulated Expression of 9-O-Acetyl GD3 (CD60b) and 7-O-Acetyl-GD3 (CD60c) During Differentiation and Maturation of Human T and B Lymphocytes. Glycobiology 2011, 21, 1161-1172.

(4) Scursoni, A. M.; Galluzzo, L.; Camarero, S.; Lopez, J.; Lubieniecki, F.; Sampor, C.; Segatori, V. I.; Gabri, M. R.; Alonso, D. F.; Chantada, G.; de Davila, M. T. Detection of N-Glycolyl GM3 Ganglioside in Neuroectodermal Tumors by Immunohistochemistry: An Attractive Vaccine Target for Aggressive Pediatric Cancer. Clin. Dev. Immunol. 2011, 2011, 245181.

(5) D'Angelo, G.; Capasso, S.; Sticco, L.; Russo, D. Glycosphingolipids: Synthesis and Functions. FEBS J. 2013, 280, 6338-6353.

(6) Schnaar, R. L.; Kinoshita, T. Glycosphingolipids. In Essentials of Glycobiology; Varki, A., Cummings, R. D., Esko, J. D., Stanley, P.; Hart, G. W., Aebi, M., Darvill, A. G., Kinoshita, T., Packer, N. H., Prestegard, J. H., Schnaar, R. L., Seeberger, P. H., Eds.; Cold Spring Harbor: NY, 2015; pp 125-135.

(7) Sonnino, S.; Chigorno, V. Ganglioside Molecular Species Containing C18- and C20-Sphingosine in Mammalian Nervous Tissues and Neuronal Cell Cultures. Biochim. Biophys. Acta 2000, 1469, 63-77.

(8) Li, Y.; Arigi, E.; Eichert, H.; Levery, S. B. Mass Spectrometry of Fluorocarbon-Labeled Glycosphingolipids. J. Mass Spectrom. 2010, 45, 504-519.

(9) Veillon, L.; Go, S.; Matsuyama, W.; Suzuki, A.; Nagasaki, M.; Yatomi, Y.; Inokuchi, J.-i. Identification of Ganglioside GM3 Molecular Species in Human Serum Associated with Risk Factors of Metabolic Syndrome. PLoS One 2015, 10, No. e0129645.

(10) Park, E. J.; Suh, M.; Ramanujam, K.; Steiner, K.; Begg, D.; Clandinin, M. T. Diet-Induced Changes in Membrane Gangliosides in Rat Intestinal Mucosa, Plasma and Brain. J. Pediatr. Gastroenterol. Nutr. 2005, 40, 487-495.

(11) Cheever, M. A.; Allison, J. P.; Ferris, A. S.; Finn, O. J.; Hastings, B. M.; Hecht, T. T.; Mellman, I.; Prindiville, S. A.; Viner, J. L.; Weiner, L. M.; Matrisian, L. M. The Prioritization of Cancer Antigens: A National Cancer Institute Pilot Project for The Acceleration of Translational Research. Clin. Cancer Res. 2009, 15, 5323-5337.

(12) Zheng, C.; Terreni, M.; Sollogoub, M.; Zhang, Y. Ganglioside GM3 and Its Role in Cancer. Curr. Med. Chem. 2019, 26, 2933-2947.

(13) Dam, D. H. M.; Paller, A. S. Gangliosides in Diabetic Wound Healing. Prog. Mol. Biol. Transl. Sci. 2018, 156, 229-239.

(14) Tagami, S.; Inokuchi, J.-i.; Kabayama, K.; Yoshimura, H.; Kitamura, F.; Uemura, S.; Ogawa, C.; Ishii, A.; Saito, M.; Ohtsuka, Y.; Sakaue, S.; Igarashi, Y. Ganglioside GM3 Participates in the Pathological Conditions of Insulin Resistance. J. Biol. Chem. 2002, 277, 3085-3092.

(15) Inamori, K.-i.; Inokuchi, J.-i. Roles of Gangliosides in Hypothalamic Control of Energy Balance: New Insights. Int. J. Mol. Sci. 2020, 21, 5349.

(16) Bremer, E. G.; Hakomori, S.; Bowen-Pope, D. F.; Raines, E.; Ross, R. Ganglioside-Mediated Modulation of Cell Growth, Growth Factor Binding, and Receptor Phosphorylation. J. Biol. Chem. 1984, 259, 6818-6825.

(17) Cutillo, G.; Saariaho, A.-H.; Meri, S. Physiology of Gangliosides and The Role of Antiganglioside Antibodies in Human Diseases. Cell. Mol. Immunol. 2020, 17, 313-322.

(18) Bremer, E. G.; Schlessinger, J.; Hakomori, S. Ganglioside-Mediated Modulation of Cell Growth. Specific Effects of GM3 on Tyrosine Phosphorylation of The Epidermal Growth Factor Receptor. J. Biol. Chem. 1986, 261, 2434-2440.

(19) Hayashi, N.; Chiba, H.; Kuronuma, K.; Go, S.; Hasegawa, Y.; Takahashi, M.; Gasa, S.; Watanabe, A.; Hasegawa, T.; Kuroki, Y.; Inokuchi, J.; Takahashi, H. Detection of N-Glycolyated Gangliosides in Non-Small-Cell Lung Cancer Using GMR8 Monoclonal Antibody. Cancer Sci. 2013, 104, 43-47.

(20) Labrada, M.; Dorvignit, D.; Hevia, G.; Rodriguez-Zhurbenko, N.; Hernandez, A. M.; Vazquez, A. M.; Fernandez, L. E. GM3-(Neu5Gc) Ganglioside: An Evolution Fixed Neoantigen for Cancer Immunotherapy. Semin. Oncol. 2018, 45, 41-51.

(21) Estevez, F.; Carr, A.; Solorzano, L.; Valiente, O.; Mesa, C.; Barroso, O.; Victoriano Sierra, G.; Fernandez, L. E. Enhancement of The Immune Response to Poorly Immunogenic Gangliosides After Incorporation into Very Small Size Proteoliposomes (VSSP). Vaccine 1999, 18, 190-197.

(22) de la Torre, A.; Perez, K.; Vega, A. M.; Santiesteban, E.; Ruiz, R.; Hernandez, L.; Durruti, D.; Viada, C. E.; Sanchez, L.; Alvarez, M.; Duran, Y.; Moreno, Y. G.; Arencibia, M.; Cepeda, M.; Domecq, M.; Cabrera, L.; Sanchez, J. L.; Hernandez, J. J.; Valls, A. R.; Fernandez, L. E. Superior Efficacy and Safety of a Nonemulsive Variant of the NGcGM3/VSSP Vaccine in Advanced Breast Cancer Patients. Breast Cancer 2016, 10, 5-11.

(23) Fernandez, L. E.; Gabri, M. R.; Guthmann, M. D.; Gomez, R. E.; Gold, S.; Fainboim, L.; Gomez, D. E.; Alonso, D. F. NGcGM3 Ganglioside: A Privileged Target for Cancer Vaccines. Clin. Dev. Immunol. 2010, 2010, 814397.

(24) Carr, A.; Rodriguez, E.; del Carmen Arango, M.; Camacho, R.; Osorio, M.; Gabri, M.; Carrillo, G.; Valdes, Z.; Bebelagua, Y.; Perez, R.; Fernandez, L. E. Immunotherapy of Advanced Breast Cancer with A Heterophilic Ganglioside (NeuGcGM3) Cancer Vaccine. J. Clin. Oncol. 2003, 21, 1015-1021.

(25) Mulens, V.; de la Torre, A.; Marinello, P.; Rodriguez, R.; Cardoso, J.; Diaz, R.; O'Farrill, M.; Macias, A.; Viada, C.; Saurez, G.; Carr, A.; Crombet, T.; Mazorra, Z.; Perez, R.; Fernandez, L. E. Immunogenicity and Safety of A NeuGcGM3 Based Cancer Vaccine: Results from A Controlled Study in Metastatic Breast Cancer Patients. Hum. Vaccines 2010, 6, 736.

(26) de la Torre, A.; Hernandez, J.; Ortiz, R.; Cepeda, M.; Perez, K.; Car, A.; Viada, C.; Toledo, D.; Guerra, P. P.; Garcia, E.; Arboláez, M.; Fernandez, L. E. NGlycolylGM3/VSSP Vaccine in Metastatic Breast Cancer Patients: Results of Phase I/IIa Clinical Trial. Breast Cancer 2012, 6, 151-157.

(27) Yu, H.; Santra, A.; Li, Y.; McArthur, J. B.; Ghosh, T.; Yang, X.; Wang, P. G.; Chen, X. Streamlined Chemoenzymatic Total Synthesis of Prioritized Glycoside Cancer Antigens. Org. Biomol. Chem. 2018, 16, 4076-4080.

(28) Santra, A.; Li, Y.; Yu, H.; Slack, T. J.; Wang, P. G.; Chen, X. Highly Efficient Chemoenzymatic Synthesis and Facile Purification of alpha-Gal Pentasaccharyl Ceramide Galalpha3nLc4betaCer. Chem. Commun. 2017, 53, 8280-8283.

(29) Koskinen, P. M.; Koskinen, A. M. P. Total Synthesis of Sphingosine and Its Analogs. Methods Enzymol. 2000, 311, 458-479.

(30) Garner, P.; Park, J. M.; Malecki, E. A Stereodivergent Synthesis of D-Erythro-Sphingosine and D-Threo-Sphingosine from L-Serine. J. Org. Chem. 1988, 53, 4395-4398.

(31) Azuma, H.; Tamagaki, S.; Ogino, K. Stereospecific Total Syntheses of Sphingosine and Its Analogues from L-Serine. J. Org. Chem. 2000, 65, 3538-3541.

(32) Gao, Y.; He, X.; Ding, F.; Zhang, Y. Recent Progress in Chemical Syntheses of Sphingosines and Phytosphingosines. Synthesis 2016, 48, 4017-4037.

(33) Hafner, A.; Duthaler, R. O.; Marti, R.; Rihs, G.; Rothe-Streit, P.; Schwarzenbach, F. Enantioselective Syntheses with Titanium Carbohydrate Complexes. Part 7. Enantioselective Allyltitanation of Aldehydes with Cyclo-

(34) Boons, G. J. P. H.; van Delft, F. L.; van der Klein, P. A. M.; van der Marel, G. A.; van Boom, J. H. Synthesis of 1d-Hepp and KDO Containing Di- and Tetrasaccharide Derivatives of *Neisseria meningitidis* Inner-Core Region via Iodonium Ion Promoted Glycosidations. Tetrahedron 1992, 48, 885-904.

(35) Dondoni, A.; Perrone, D. Synthesis of 1,1-Dimethylethyl (S)-4-Formyl-2,2-Dimethyl-3-Oxazolidinecarboxylate by Oxidation of The Alcohol. Org. Synth. 2000, 77, 64-77.

(36) Yoshida, M.; Saito, K.; Kato, H.; Tsukamoto, S.; Doi, T. Total Synthesis and Biological Evaluation of Siladenoserinol A and Its Analogues. Angew. Chem., Int. Ed. 2018, 57, 5147-5150.

(37) Ghosh, A.; Chattopadhyay, S. K. A Diversity Oriented Synthesis of D-Erythro-Sphingosine and Siblings. Tetrahedron: Asymmetry 2017, 28, 1139-1143.

The complete disclosure of all patents, patent applications, and publications, and electronically available material cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The disclosure is not limited to the exact details shown and described, for variations obvious to one skilled in the art will be included within the disclosure defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present disclosure. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The invention claimed is:

1. A compound of the following structure:

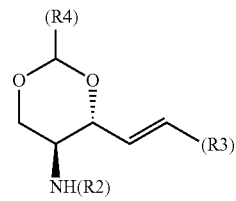

wherein R2 is independently a protecting group,
wherein R3 is an aliphatic group of at least 2 to no greater than 36 carbons, and
wherein R4 is independently a protecting group, wherein the protecting group is not a benzyl group.

2. The compound of claim 1, wherein R3 is C13H27.

3. A compound of the following structure:

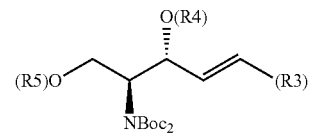

wherein R3 is an aliphatic group of at least 2 to no greater than 36 carbons,
wherein R4 is H, or a protecting group, and
wherein R5 is H, a glycan, phosphorylethanolamine, or phosphorylcholine.

4. The compound of claim 3, wherein R3 is $C_{13}H_{27}$.

5. The compound of claim 3, wherein R5 has the following structure:

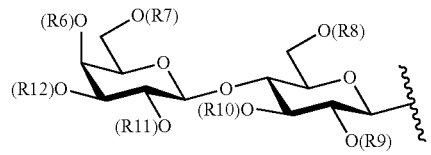

wherein R5, R6, R7, R8, R9, R10, R11, and R12 are each independently a protecting group.

6. A composition comprising of a mixture of D-erythro and L-threo isomers having the following structure:

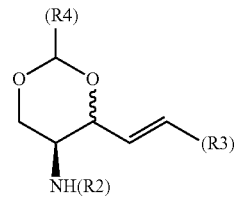

wherein R2 is a protecting group,
wherein R3 is an aliphatic group of at least 2 to no greater than 36 carbons, and
wherein R4 is independently a protecting group, wherein the protecting group is not a benzyl group, and wherein the D-erythro isomer having the following structure:

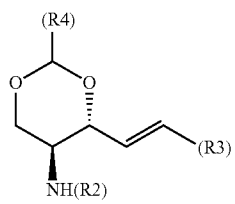

is present in the composition in at least 70% enantiomeric excess.

7. A method for synthesizing D-erythro-sphingosine, comprising:
(a) reacting a first mixture of diastereomers having the following structure:

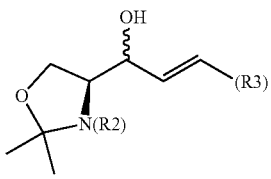

wherein R2 is a protecting group,
wherein R3 is $C_{13}H_{27}$, and
wherein the reacting comprises conditions suitable for formation of a mixture of D-erythro and L-threo isomers having the following structure:

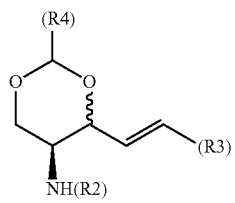

wherein R4 is a protecting group,
(b) purifying the protected D-erythro isomer from the mixture of protected D-erythro and protected L-threo isomers, and
(c) deprotecting the protected D-erythro isomer to result in D-erythro-sphingosine.

8. The method of claim 7, wherein the purifying comprises crystallization.

9. A method for synthesizing an acceptor compound, comprising:
(a) reacting the compound of the following structure:

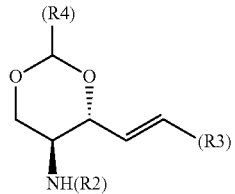

wherein R2 is independently a protecting group,
wherein R3 is an aliphatic group of at least 2 to no greater than 36 carbons, and wherein R4 is independently a protecting group, wherein the protecting group is not a benzyl group,
wherein the reacting comprises conditions suitable for converting NH(R2) to NBoc$_2$, and
(b) opening the 6-membered heterocyclic ring to result in an acceptor compound having the following structure:

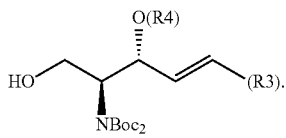

10. The method of claim 9, wherein R3 is $C_{13}H_{27}$.

11. A method for synthesizing a compound comprising a 6-membered heterocyclic ring and having the following formula:

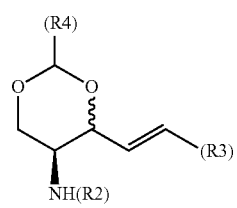

wherein R2 and R4 are each independently a protecting group, and
wherein R3 is an aliphatic group of at least 2 to no greater than 36 carbons, the method comprising reacting a compound of the following formula:

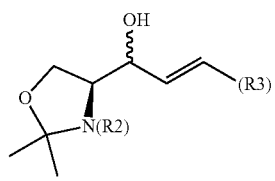

wherein the reacting comprises a deprotecting step followed by forming the 6-membered heterocyclic ring to prevent free bond rotation around C2 and C3.

12. The method of claim 11, wherein R3 is $C_{13}H_{27}$.

13. A method for making a glycolipid comprising:
providing the compound of claim 3, wherein R5 is H, and
glycosylating the compound by linking a glycan comprising a reducing end to the free hydroxyl of the compound to yield a protected glycolipid having the following structure:

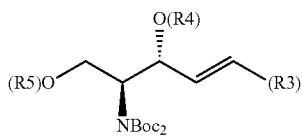

wherein R5 is the glycan.

14. The method of claim 13, further comprising deprotecting the protected glycolipid.

15. The method of claim 13, wherein R3 is C13H27 and wherein R5 is lactose.

16. A method for making lactosyl β-sphingosine, comprising deprotecting the compound of claim 5,
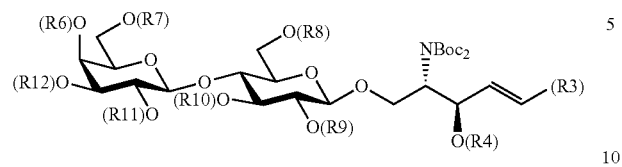
wherein R4, R5, R6, R7, R8, R9, R10, R11, and R12 are each independently a protecting group.
* * * * *